US012648942B2

(12) United States Patent
Chou et al.

(10) Patent No.: US 12,648,942 B2
(45) Date of Patent: Jun. 9, 2026

(54) METHOD FOR TREATING ACUTE ISCHEMIC STROKE

(71) Applicant: Lumosa Therapeutics Co., LTD, Taipei (TW)

(72) Inventors: David Chih-Kuang Chou, Taipei (TW); Jung-Chin Lin, Taipei (TW); Sheng-Wen Yeh, Taipei (TW); Shiqi Peng, Beijing (CN); Ming Zhao, Beijing (CN)

(73) Assignee: LUMOSA THERAPEUTICS CO., LTD., Taipei (TW)

( * ) Notice: Subject to any disclaimer, the term of this patent is extended or adjusted under 35 U.S.C. 154(b) by 404 days.

(21) Appl. No.: 18/470,988

(22) Filed: Sep. 20, 2023

(65) Prior Publication Data

US 2024/0016794 A1     Jan. 18, 2024

Related U.S. Application Data

(63) Continuation of application No. PCT/CN2022/082100, filed on Mar. 21, 2022.

(60) Provisional application No. 63/164,336, filed on Mar. 22, 2021.

(51) Int. Cl.
| | |
|---|---|
| *A61K 31/4725* | (2006.01) |
| *A61K 31/4365* | (2006.01) |
| *A61K 31/4439* | (2006.01) |
| *A61K 31/4545* | (2006.01) |
| *A61K 31/616* | (2006.01) |
| *A61P 9/10* | (2006.01) |

(52) U.S. Cl.
CPC ...... *A61K 31/4725* (2013.01); *A61K 31/4365* (2013.01); *A61K 31/4439* (2013.01); *A61K 31/4545* (2013.01); *A61K 31/616* (2013.01); *A61P 9/10* (2018.01)

(58) Field of Classification Search
CPC ............ A61K 31/4439; A61K 31/4545; A61K 38/07; A61P 9/10
See application file for complete search history.

(56) References Cited

U.S. PATENT DOCUMENTS 10,351,594 B2 *   7/2019   Peng ......................... A61P 9/10

OTHER PUBLICATIONS

Kuo, Tun-Hsun, et al. "A Novel Dual Function Molecule for the Treatment of Acute Ischemic Stroke." Stroke 47.suppl_1 (2016): A173-A173. (Year: 2016).*
Wilterdink, Janet L., et al. "Effect of prior aspirin use on stroke severity in the trial of Org 10172 in acute stroke treatment (TOAST)." Stroke 32.12 (2001): 2836-2840. (Year: 2001).*
Fluri, Felix, Michael K. Schuhmann, and Christoph Kleinschnitz. "Animal models of ischemic stroke and their application in clinical research." Drug design, development and therapy (2015): 3445-3454. (Year: 2015).*
International Search Report, PCT/CN2022/082100, Jun. 22, 2022.
Feng, Qiqi et al., DHDMIQK(KAP): a novel nano-delivery system of dihydroxyl-tetrahydro-isoquinoline-3-carboxylic acid and KPAK towards the thrombus, Journal of Materials Chemistry, Aug. 16, 2016, pp. 5991-6003, vol. 1, No. 36, The Royal Society of Chemistry.
Lumosa Therapeutics Co., Ltd., A Study to Evaluate the Safety and Potential Efficacy of LT3001 Drug Product in Subjects with AIS, Jan. 1, 2019, National Library of Medicine.

* cited by examiner

*Primary Examiner* — Lianko G Garyu
*Assistant Examiner* — David Paul Bowles
(74) *Attorney, Agent, or Firm* — PERKINS COIE LLP; Viola T. Kung

(57) ABSTRACT

The present invention is directed to a method of treating acute ischemic stroke in a human comprising administering one of more low doses of DC009, wherein the dose is about 0.01-0.075 mg/kg/dose. The low dose administration is safe and effective in treating acute ischemic stroke in a human subject.

13 Claims, 6 Drawing Sheets

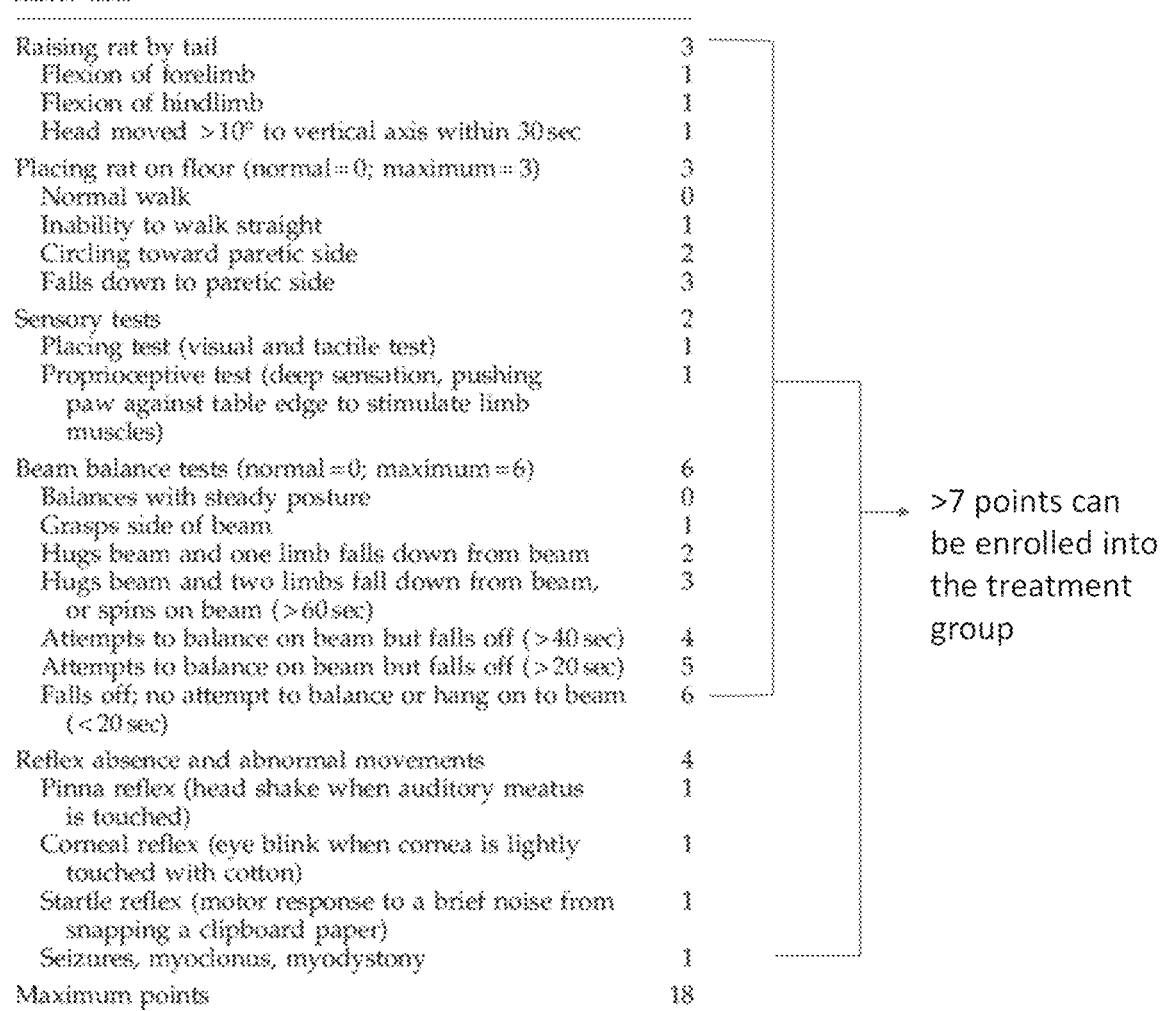

| *Motor tests* | |
|---|---|
| Raising rat by tail | 3 |
|   Flexion of forelimb | 1 |
|   Flexion of hindlimb | 1 |
|   Head moved >10° to vertical axis within 30 sec | 1 |
| Placing rat on floor (normal = 0; maximum = 3) | 3 |
|   Normal walk | 0 |
|   Inability to walk straight | 1 |
|   Circling toward paretic side | 2 |
|   Falls down to paretic side | 3 |
| Sensory tests | 2 |
|   Placing test (visual and tactile test) | 1 |
|   Proprioceptive test (deep sensation, pushing paw against table edge to stimulate limb muscles) | 1 |
| Beam balance tests (normal = 0; maximum = 6) | 6 |
|   Balances with steady posture | 0 |
|   Grasps side of beam | 1 |
|   Hugs beam and one limb falls down from beam | 2 |
|   Hugs beam and two limbs fall down from beam, or spins on beam (>60 sec) | 3 |
|   Attempts to balance on beam but falls off (>40 sec) | 4 |
|   Attempts to balance on beam but falls off (>20 sec) | 5 |
|   Falls off; no attempt to balance or hang on to beam (<20 sec) | 6 |
| Reflex absence and abnormal movements | 4 |
|   Pinna reflex (head shake when auditory meatus is touched) | 1 |
|   Corneal reflex (eye blink when cornea is lightly touched with cotton) | 1 |
|   Startle reflex (motor response to a brief noise from snapping a clipboard paper) | 1 |
|   Seizures, myoclonus, myodystony | 1 |
| Maximum points | 18 |

>7 points can be enrolled into the treatment group

FIG. 2

P<0.01, DC009 versus tPA; *P<0.001, DC009 versus saline

| Example | Animal model | Content | Rat dose |
|---|---|---|---|
| 1 | Rat model 1 | Embolic stroke model | N/A |
| 2 | Rat model 2 | MCAO model | N/A |
| 3 | Rat model 3 | PIT stroke model | N/A |
| 4 | Embolic stroke model | single dose, 3 hr post-AIS | 0.007 *mg/kg/dose |
| 5 | Embolic stroke model | single dose, 6 hr post-AIS | 0.007* mg/kg/dose |
| 6 | Embolic stroke model | 6 days (one dose /day), 24 hr post-AIS | 0.0007, 0.007*, 0.07* mg/kg/dose |
| 7 | MCAO model | single dose, 3 hr post-AIS | 0.005*, 0.05*** mg/kg/dose |
| 8 | MCAO model | single dose, 1 hr post-AIS | 0.05****, 0.1****, 0.2****, 0.4**** mg/kg/dose |
| 9 | MCAO model | 2 dose/day, 3 hr and 6 hr post-AIS | 0.025*** mg/kg/dose |
| 10 | PIT stroke model | single dose, 1 hr / 3 hr post-AIS | 0.007** mg/kg/dose |

* indicates p value < 0.05,  indicates p value < 0.01, * indicates p value < 0.001, **** indicates p value < 0.0001, all vs. saline

FIG. 5

| DC009 | Placebo | P value |
|---|---|---|
| -4.3 ± 3 | 3.5 ± 2.1 | P=0.007 |

| Example | Human trial | Administration | Dose | $C_{max}$ | Efficacy |
|---|---|---|---|---|---|
| 11 | Phase I -101 | single dose | 0.025, 0.05 mg/kg/dose | 59.9 ± 4.7, 90.9 ±17.9ng/mL | N/A |
| 12 | Phase I-103 | 3 days (2 dose/day) | 0.025, 0.05 mg/kg/dose | 56.8±14.5, 57.3±11.0 ng/mL (5th dose) | N/A |
| 13 | Phase I- 105 | 3 days (3 dose/day) | 0.025 mg/kg/dose | 48.86 ±17.06 ng/mL (Day 3) | N/A |
| 14 | Phase II- 201 | single dose, within 24 hr post-AIS | 0.025 mg/kg/dose | | p= 0.007 vs placebo |
| 15 | Phase II-202 | 3 days (2 dose/day) | 0.025, 0.05 mg/kg/dose | | |
| 16 | Phase II- 203 | 3 days (2 dose/day) | 0.025 mg/kg/dose | | |
| 17 | Phase II- 205 | 3 days (2 dose/day) | 0.05 mg/kg/dose | | |

FIG. 7

METHOD FOR TREATING ACUTE ISCHEMIC STROKE

This application is a continuation of PCT/CN2022/082100, filed Mar. 21, 2022; which claims the benefit of U.S. Provisional Application No. 63/164,336, filed Mar. 22, 2021. The contents of the above-identified applications are incorporated herein by reference in their entirety.

FIELD OF THE INVENTION

This invention relates to a method of treating acute ischemic stroke in humans using a low dose of 3S-6,7-dihydroxy-1,1-dimethyl-1,2,3,4-tetrahydro-isoquinoline-3-acyl-Lys(Pro-Ala-Lys) (CAS RN: 1639303-73-3).

BACKGROUND OF THE INVENTION

Stroke is classically characterized as a neurological deficit attributed to an acute focal injury of the central nervous system by a vascular cause. Ischemic strokes account for about 87% of all strokes; 10% are intracerebral hemorrhage strokes, whereas 3% are subarachnoid hemorrhage strokes. Annually, 15 million people worldwide suffer a stroke; in the United States, on average, someone experiences a stroke every 40 seconds. Globally, stroke is the second leading cause of death above the age of 60 years and is the leading cause of disability.

Alteplase (Activase®), a recombinant tissue-type plasminogen activator (rtPA), was the first medication approved for the treatment of ischemic stroke by the US Food and Drug Administration in 1996 (BLA 103172/S-1055). Although alteplase has been shown to improve the outcome of subjects with acute ischemic stroke (AIS), its use has been limited as it is approved for administration only within 3 hours (in the United States) or 4.5 hours after symptom onset, and it causes nearly 5-fold risk of symptomatic intracerebral hemorrhage.

Due to the above-mentioned reasons, the usage rate of alteplase is low, and only approximately 5% of stroke patients are administered alteplase. As such, there is a need to develop treatments that can offer similar efficacy to alteplase but with a lower increase of bleeding and/or a longer therapeutic window.

DC009 is a peptide-tetrahydroisoquinoline conjugate, which has a chemical name of 3S-6,7-dihydroxy-1,1-dimethyl-1,2,3,4-tetrahydro-isoquinoline-3-acyl-Lys(Pro-Ala-Lys) or L-Lysine, N6-(L-prolyl-L-alanyl-L-lysyl)-N2-[[(3S)-1,2,3,4-tetrahydro-6,7-dihydroxy-1,1-dimethyl-3-isoquinolinyl]carbonyl] (CAS RN: 1639303-73-3). DC009 is a binary conjugate that can be formed by coupling a thrombolytic peptide (Pro-Ala-Lys) and a tetrahydroisoquinoline compound having two C1-4 alkyl groups via a Lysine linking arm. The structure of DC009 is shown in FIG. A, the amide bond between the Lysine linking arm and the Pro-Ala-Lys peptide is shown in FIG. 1B.

Pharmaceutical development is a stepwise process involving an evaluation of both animal and human efficacy and safety information. The goals of the non-clinical safety evaluation generally include characterization of toxic effects; this information is used to estimate an initial safe starting dose and dose range for the human trials and to identify parameters for clinical monitoring for potential adverse effects. All relevant preclinical data, including information on the pharmacologically active dose, the full toxicologic profile of the compound, and the pharmacokinetics (absorption, distribution, metabolism, and excretion) of the therapeutic, should be considered.

Maximum recommended starting dose (MRSD) for first-in-human clinical trials of new molecular entities in adult healthy volunteers should be determined by dividing the human equivalent dose (HED) derived from the animal no observed adverse effect levels (NOAEL) by a safety factor. The default safety factor normally used is 10, which is a historically accepted value, but it should be evaluated based on available information. This is a non-binding recommendation by FDA and Center for Drug Evaluation and Research (CDER). However, a safety factor of 10 may not be appropriate for all cases. The safety factor should be raised when there is reason for increased concern, and lowered when concern is reduced because of available data that provide added assurance of safety. (Guidance for Industry "Estimating the Maximum Safe Starting Dose in Initial Clinical Trials for Therapeutics in Adult Healthy Volunteers", www.fda.gov/media/72309/download)

The development of therapies for acute ischemic stroke (AIS) is a difficult and challenging endeavor, due to the complexity of the pathophysiology and clinical aspects of this heterogeneous disorder. Recombinant Tissue Plasminogen Activator (rtPA) initiated within 3 hours of stroke onset is the only one currently approved therapy for AIS. There are only limited track records to assess the use of animal models in the development of AIS therapies. A large number of interventions demonstrated efficacy in animal models of AIS and these interventions, primarily neuroprotective agents, have not been shown to improve AIS outcome in patient (Fisher, al, Stroke. Volume 36, Issue 10, 1 Oct. 2005; Pages 2324-2325). The discrepancy in results regarding neuroprotective agents in animal experiments compared to clinical trials is a major problem. While many neuroprotective agents have been proven effective in a variety of animal ischemic stroke models, none have been shown to work in clinical trials (Xu, et al, Med Sci Monit Basic Res. 2013 Jan. 28; 19:37-45. doi: 10.12659/msmbr.883750).

There exists a need for a method for treated acute ischemic stroke. The method should be effective and with minimal side effects or toxicity.

BRIEF DESCRIPTION OF THE DRAWINGS

FIG. 1A shows the chemical structure of DC009. FIG. 1B shows the chemical structure of DC009 with the detail of NH-Lys-Ala-Pro.

FIG. 2 shows the method for Neurological deficits assessment.

FIG. 5 summarizes Examples 1-10 (rat model).

FIG. 7 summarizes Examples 11-16 (human clinical trial results or protocols).

DETAILED DESCRIPTION OF THE INVENTION

Figure 3:
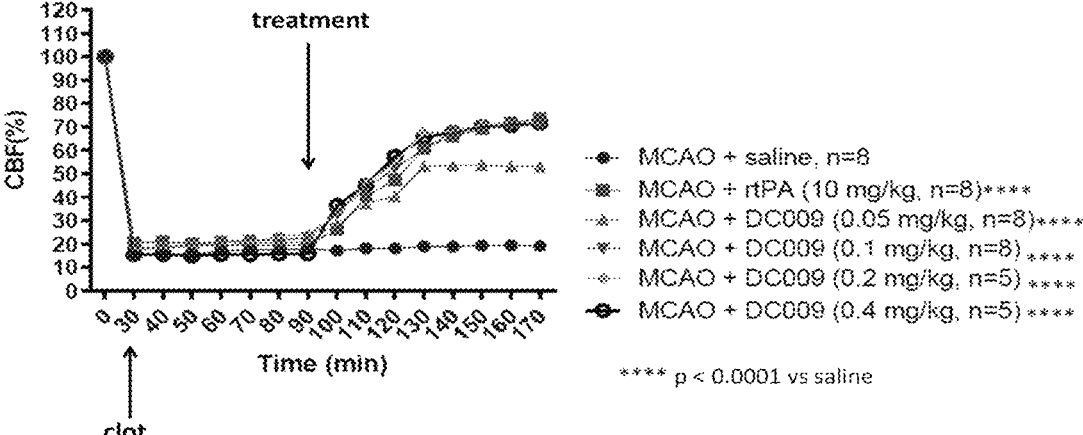
FIG. 3 shows the blood flow result for single dose of DC009 in rat MCAO model.

In view of thrombolytic and free radical scavenging effects of DC009 in rat, the inventors have discovered a method for treating acute ischemic stroke in a human subject. The method comprises administering an effective amount of DC009, or a pharmaceutical acceptable salt thereof, to the subject in need thereof, wherein the amount of DC009 is effective to treat the disease and provides a safe $C_{max}$ with minimal observed adverse effect levels. The present method provides a proper dosage; the dosage is effective in treating acute ischemic stroke in a human subject and provides a minimal risk of bleeding and a potentially extended treatment time window.

According to inventors' pre-clinical toxicity result of DC009 in minipig, the inventors set up a limit on plasma exposure of 1177 ng/mL in minipigs. The inventors then set up a safety factor to provide a margin of safety for protecting human subjects receiving the initial clinical dose. As described in the Background, the default safety factor is 10 but it may be adjusted based on available safety data. In the present invention, administration of DC009 in a human subject is limited to doses resulting in plasma $C_{max}$ no more than about 200 ng/mL, and preferably no more than about 150 ng/mL or no more than about 110 ng/mL.

The inventors have discovered that an effective and safe amount of DC009 for treating acute ischemic stroke in a human subject is a low dose of about 0.01-0.075 mg/kg/dose, or about 0.025-0.05 mg/kg/dose. For example, an effective and safe dose is about 0.025 mg/kg/dose, or about 0.05 mg/kg/dose.

"About", as used throughout this application, refers to +10% of recited value.

The inventors have discovered that the present low dose of DC009 is effective in treating acute ischemic stroke and provides low plasma drug level, which reduces potential drug toxicity. The elimination half-life of DC009 is extremely short (elimination half-life <5 minutes), and DC009 is eliminated from circulation shortly after dosing, which is almost un-measurable in human plasma after 30 minutes after dosing. Administration of multiple doses of DC009 does not lead the accumulation of DC009, and the therapeutic efficacy of DC009 is achieved via the drug exposure of each dose.

Figures 1A, 1B:
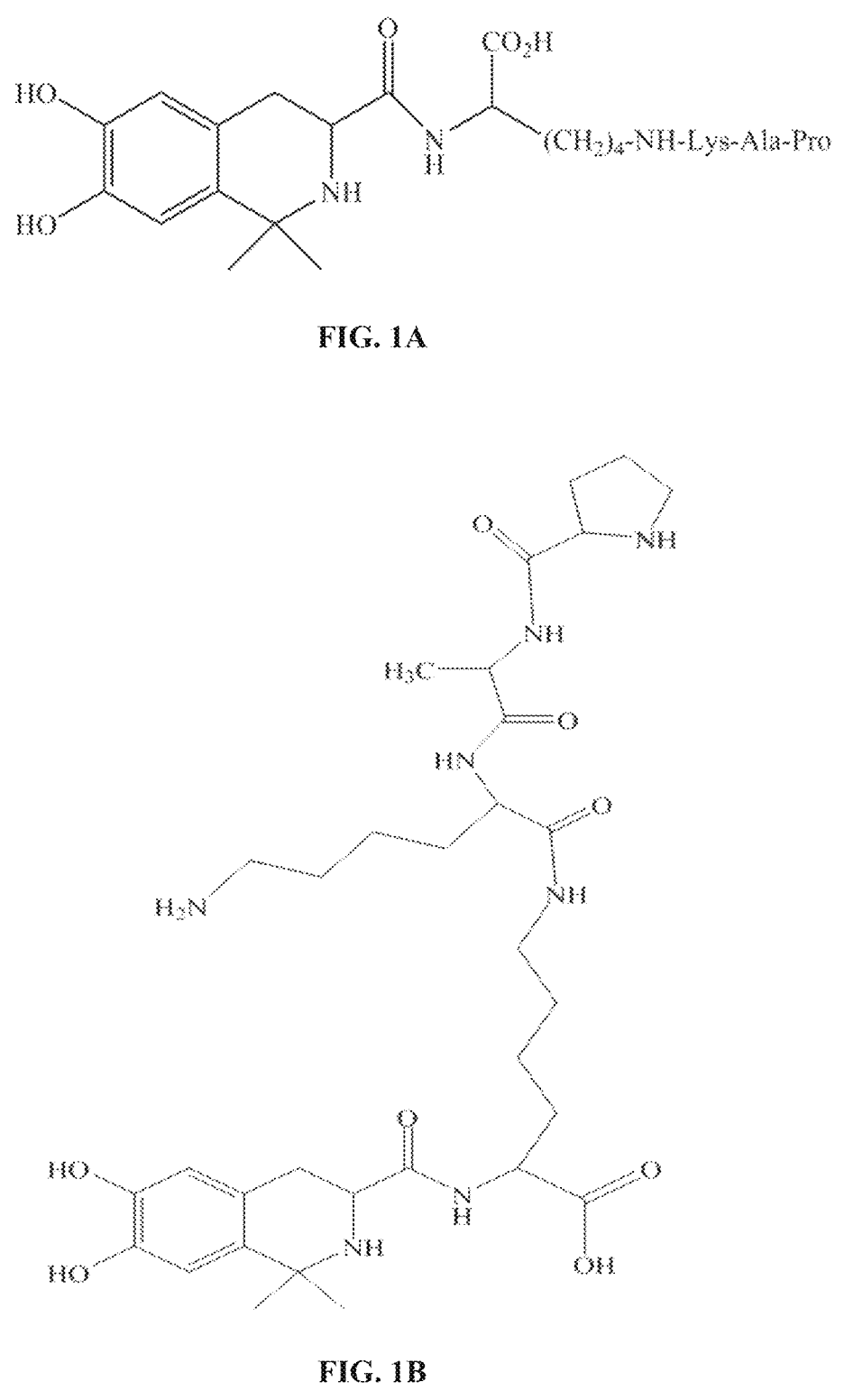

A pharmaceutical acceptable salt of DC009 (see FIGS. 1A and 1B) includes any salt that are pharmaceutically acceptable; for example, a hydrochloride salt, i.e. L-lysine, N6-(L-prolyl-L-alanyl-L-lysyl)-N2-[[(3S)-1,2,3,4-tetrahydro-6, 7-dihydroxy-1,1-dimethyl-3-isoquinolinyl]carbonyl]-hydrochloride (1:3) (CAS RN: 2419930-71-3). The molecular formula of DC009 is C32H51N7O8, and the molecular weight of free base is 661.8 g/mole.

The preparation of the DC009 compound is disclosed in Example 63 of US Publication No. 2016-0083423, which is incorporated herein by reference. The present invention uses pharmaceutical compositions comprising one or more pharmaceutically acceptable carriers and the DC009 compound, or a pharmaceutically acceptable salt thereof.

Pharmaceutically acceptable carriers, which are inactive ingredients, can be selected by those skilled in the art using conventional criteria. Pharmaceutically acceptable carriers may contain ingredients that include, but are not limited to, saline and aqueous electrolyte solutions; ionic and nonionic osmotic agents such as sodium chloride, potassium chloride, glycerol, and dextrose; pH adjusters and buffers such as salts of hydroxide, phosphate, citrate, acetate, borate; and trolamine; antioxidants such as salts, acids and/or bases of bisulfite, sulfite, metabisulfite, thiosulfite, ascorbic acid, acetyl cysteine, cysteine, glutathione, butylated hydroxyanisole, butylated hydroxytoluene, tocopherols, and ascorbyl palmitate; surfactants such as lecithin, phospholipids, including but not limited to phosphatidylcholine, phosphatidylethanolamine and phosphatidyl inositiol; poloxamers and poloxamines, polysorbates such as polysorbate 80, polysorbate 60, and polysorbate 20, polyethers such as polyethylene glycols and polypropylene glycols; polyvinyls such as polyvinyl alcohol and povidone; cellulose derivatives such as methylcellulose, hydroxypropyl cellulose, hydroxyethyl cellulose, carboxymethyl cellulose and hydroxypropyl methylcellulose and their salts; polymers of acrylic acid such as carboxypolymethylene gel, and hydrophobically modified cross-linked acrylate copolymer; polysaccharides such as dextrans and glycosaminoglycans such as sodium hyaluronate. Such pharmaceutically acceptable carriers may be preserved against bacterial contamination using well-known preservatives, these include, but are not limited to, benzalkonium chloride, ethylenediaminetetraacetic acid and its salts, benzethonium chloride, chlorhexidine, chlorobutanol, methylparaben, thimerosal, and phenylethyl alcohol, or may be formulated as a non-preserved formulation for either single or multiple use.

One of the pharmaceutical compositions for human use is a lyophilized powder comprising the hydrochloride salt of DC009 (C32H51N7O8·3HCl); the main excipient is mannitol. DC009 is further diluted to suitable concentration with normal saline before administration.

In some embodiments, the dose of DC009 for treating acute ischemic stroke in a human subject is about 0.01-0.075 mg/kg/dose. In some embodiments, the dose of DC009 for treating acute ischemic stroke in a human subject is about 0.025-0.05 mg/kg/dose. In one embodiment, the dose of DC009 for treating acute ischemic stroke in a human subject is about 0.025 mg/kg/dose. In one embodiment, the dose of DC009 for treating acute ischemic stroke in a human subject is about 0.05 mg/kg/dose.

In some embodiments, the dose is administered at least once per day. In some embodiments, the dose is administered once per day. In some embodiments, the dose is administered twice a day. In some embodiments, the dose is administered three times a day. As used throughout this application, the dose refers to the dose of DC009.

In some embodiments, the dose is administered at dosage intervals of about 3-12 hours. In some embodiments, the dose is administered at dosage intervals of 3, 4, 5, 6, 7, 8, 9, 10, 11 or 12 hours. In some embodiments, the dose is administered at dosage intervals of about 3 hours, 6 hours, 9 hours or 12 hours. In some embodiments, the dose is administered at dosage intervals of about 3 hours. In some embodiments, the dose is administered at dosage intervals of about 6 hours. In some embodiments, the dose is administered at dosage intervals of about 12 hours.

In some embodiments, the dose is administered to the subject for 1-6 days. For example, the dose is administered to the subject for 1, 2, 3, 4, 5 or 6 days. In one embodiment, the dose is administered to the subject for 1 day. In one embodiment, the dose is administered to the subject for 2 days. In one embodiment, the dose is administered to the subject for 3 days. In one embodiment, the dose is administered to the subject for 4 days. In one embodiment, the dose is administered to the subject for 5 days. In one embodiment, the dose is administered to the subject for 6 days. In some embodiments, the dose is administered to the subject once to three times a day for 1-6 days. In one embodiment, the dose is administered to the subject three times a day for 3 days. In one embodiment, the dose is administered to the subject twice a day for 3 days. In one embodiment, the dose is administered to the subject twice a day for 6 days. In one embodiment, the dose is administered to the subject once per day for 6 days.

In one embodiment, the dose is about 0.025 mg/kg/dose, and is administered to the subject at a single dose. In one embodiment, the dose is about 0.05 mg/kg/dose, and is administered to the subject at single dose.

In one embodiment, the dose is about 0.025 mg/kg/dose, and is administered to the subject twice a day for 3 days. In one embodiment, the dose is about 0.05 mg/kg/dose, and is administered to the subject twice a day for 3 days. In one embodiment, the dose is about 0.025 mg/kg/dose, and is administered to the subject three times a day for 3 days. In one embodiment, the dose is about 0.05 mg/kg/dose, and is administered to the subject three times a day for 3 days.

In some embodiments, the compound or the pharmaceutical composition is administered to the subject immediately, or within 1-24 hours, or within 3-24 hours after the onset of acute ischemic stroke. In one embodiment, the compound or the pharmaceutical composition is administered to the subject immediately after the onset of acute ischemic stroke. In one embodiment, the compound or the pharmaceutical composition is administered to the subject within 1-24 hours after the onset of acute ischemic stroke. In one embodiment, the compound or the pharmaceutical composition is administered to the subject within 3-24 hours after the onset of acute ischemic stroke. In some embodiments, the compound or the pharmaceutical composition is administered to the subject within 3 hours, 6 hours, 9 hours, or 24 hours after the onset of acute ischemic stroke. In some embodiments, the compound or the pharmaceutical composition is administered to the subject within 3 hours after the onset of acute ischemic stroke. In some embodiments, the compound or the pharmaceutical composition is administered to the subject within 24 hours after the onset of acute ischemic stroke.

The National Institute of Health Stroke Scale (NIHSS) is a predictor for the prognosis of acute ischaemic stroke (AIS) and its prediction is time-dependent. In some embodiments, the AIS patient suitable for treating by the present invention has a NIHSS of 4-30. In some embodiments, the AIS patient has a NIHSS of 4-25. In some embodiments, the AIS patient has a NIHSS of 6-25. In some embodiments, the AIS patient has a NIHSS of 6-12. In some embodiments, the AIS patient has a NIHSS of 13-25. In some embodiments, the AIS patient has a NIHSS of ≥6. In some embodiments, the AIS patient has a NIHSS of ≥4.

In some embodiments, the AIS patient has a large artery atherosclerosis.

In some embodiments, the AIS patient has an age less than 65. In some embodiments, the AIS patient has an age less than 80. In some embodiments, the AIS patient has an age greater than 65. In some embodiments, the AIS patient has an age greater than 80.

In some embodiments, the AIS patient has a stroke symptoms onset within 6 hours. In some embodiments, the AIS patient has a stroke symptoms onset within 9 hours. In some embodiments, the AIS patient has a stroke symptoms onset within 12 hours. In some embodiments, the AIS patient has a stroke symptoms onset within 16 hours. In some embodiments, the AIS patient has a stroke symptoms onset greater than 16 hours.

In some embodiments, the AIS patient has a symptomatic intracranial occlusion at M1 middle cerebral artery. In some embodiments, the AIS patient has a symptomatic intracranial occlusion at M2 middle cerebral artery.

In some embodiments, the AIS patient has a mismatch profile on MRI (magnetic resonance imaging) or CTP (computed tomography perfusion): ischemic core volume ≤70 mL, mismatch ratio >1.2 and mismatch volume ≥5 mL. In some embodiments, the AIS patient has an ischemic core ≤20 mL. In some embodiments, the AIS patient has an ischemic core ≤30 mL. In some embodiments, the AIS patient has an ischemic core ≤50 mL.

In some embodiments, the AIS patient has a mismatch ratio >1.8. In some embodiments, the AIS patient has a mismatch volume >10 mL. In some embodiments, the AIS patient has a mismatch volume >20 mL.

An intravenous (IV) injection delivers a pharmaceutical composition to the bloodstream, where the composition can be absorbed quickly and with maximum effectiveness. Intravenous administration therapeutic agent can be given via push, bolus or given via a continuous infusion. An intravenous push (IV push) is administered within 30 seconds to achieve this rapid response; IV push does not rely on a drip bag. Intravenous bolus (IV bolus) is easy to perform which do not require infusion pump. Intravenous infusion (IV infusion) takes longer time to administrate the agent while providing a steady state concentration of the therapeutic agent.

In some embodiments, the present pharmaceutical composition comprising the DC009 compound is administered by intravenous infusion. In some embodiments, the present pharmaceutical composition is administered by intravenous infusion over a period of 5-60 minutes. In some embodiments, the present pharmaceutical composition is administered by intravenous infusion over a period of 15-30 minutes. In one embodiment, the pharmaceutical composition is administered by intravenous infusion over a period of 15 minutes. In some embodiments, the pharmaceutical composition is administered by intravenous infusion over a period of 30 minutes.

In some embodiments, the pharmaceutical composition is administered by intravenous bolus injection.

In some embodiment, the pharmaceutical composition is administered by intravenous bolus injection followed with intravenous infusion.

In some embodiments, the pharmaceutical composition was administered to AIS patient by any accessible vein.

In one example, the dose is about 0.05 mg/kg/dose, and the pharmaceutical composition is administered by intravenous infusion over a period of 30 minutes.

In another example, the dose is about 0.025 mg/kg/dose, and the pharmaceutical composition is administered by intravenous infusion over a period of 15 minutes.

In another example, the dose is about 0.025 mg/kg/dose, and the pharmaceutical composition is administered by intravenous infusion over a period of 30 minutes, In some embodiments, the pharmaceutical composition is co-administered with aspirin, clopidogrel, apixaban, or dabigatran. In one embodiment, the pharmaceutical composition is co-administered with aspirin. In one embodiment, the pharmaceutical composition is co-administered with clopidogrel. In one embodiment, the pharmaceutical composition is co-administered with apixaban. In one embodiment, the pharmaceutical composition is co-administered with dabigatran.

In some embodiments, the human subject is administered before, during or after endovascular thrombectomy. In some embodiments, the human subject is administered before endovascular thrombectomy. In some embodiments, the human subject is administered b during endovascular thrombectomy. In some embodiments, the human subject is administered before, after endovascular thrombectomy.

In some embodiments, endovascular thrombectomy and administration of DC009 are both occurred within 24 hours of stroke onset.

In some embodiments, the plasma drug level of the human subject during the treating period is less than 200 ng/mL. In some embodiments, the plasma drug level of the human subject during the treating period is less than 150 ng/mL. In some embodiments, the plasma drug level of the human subject during the treating period is less than 110 ng/mL.

The efficacy outcome of DC009 can be evaluated by neurological outcomes, such as the change of NIHSS at a specific period after dosing. In some embodiments, the AIS patient has a decrease ≥4 in the NIHSS from Baseline. In some embodiments, the AIS patient has a decrease ≥8 in the NIHSS from Baseline. In some embodiments, the AIS patient resulted as NIHSS ≤2 after dosing. In some embodiments, the AIS patient resulted as NIHSS≤4 after dosing.

The efficacy outcome of DC009 can be evaluated by functional outcomes, such as the change of Modified Rankin Scale (mRS) at a specific period after dosing. In some embodiments, the AIS patient has a decrease >1 in mRS from Baseline. In some embodiments, the AIS patient resulted as mRS 0-2 after treatment. In some embodiments, the AIS patient resulted as mRS 0-1 after treatment.

The efficacy outcome of DC009 can be evaluated by functional outcomes, evaluated by Barthel Index at a specific period after dosing.

The efficacy outcome of DC009 can be evaluated by imaging outcomes, such as the change of infarct volume from Baseline by MRI/CTP, the change of hypoperfusion lesion from Baseline by perfusion-weight imaging RI/CTP. In some embodiments, the AIS patient resulted as less infarct growth by 10%. In some embodiments, the AIS patient resulted as less infarct growth by 20%.

In some embodiments, the AIS patient treated with DC009 resulted as more patients achieve >50% reperfusion by 10%, 20% or 30% compared to non-treatment. In some embodiments, the AIS patient treated with DC009 resulted as more patients achieve >90% reperfusion by 10%, 20% or 30% compared to non-treatment. In some embodiments, the AIS patient treated with DC009 resulted as more patients achieve recanalization by 10%, 20% or 30% compared to non-treatment.

In summary, the present invention is directed to a method for treating acute ischemic stroke in a human subject, comprising administering the DC009 compound to the subject in need thereof, wherein the dose is about 0.01-0.075 mg/kg/dose. In one embodiment, the dose is about 0.025-0.05 mg/kg/dose. In one embodiment, the dose is about 0.025 mg/kg/dose. In another embodiment, the dose is about 0.05 mg/kg/dose.

In the present method, the compound is administered at least once per day. In one embodiment, the compound is administered twice a day. In another embodiment, the compound is administered at dosage intervals of about 3-12 hours. In another embodiment, the compound is administered at least once per day for 2 days or for 3 days. In yet another embodiment, the compound is administered at least twice a day for 3 days. In yet another embodiment, the compound is administered at dosage intervals of about 12 hours.

In the present method, the compound is administered to the subject immediately or within 1-24 hours after the onset of acute ischemic stroke.

In the present method, the compound is administered by intravenous infusion and/or bolus injection. In one embodiment, the compound is administered by intravenous infusion. In one embodiment, the compound is administered by intravenous infusion over a period of 5-60 minutes.

In the present method, the compound may be co-administered with aspirin, clopidogrel, apixaban or dabigatran.

In the present method, the Cmax in the plasma of the subject after dosing is less than 200 ng/mL. In some embodiments, the Cmax in the plasma of the subject after dosing is less than 150 ng/mL.

The following examples further illustrate the present invention. These examples are intended merely to be illustrative of the present invention and are not to be construed as being limiting.

EXAMPLES

List of Abbreviations

| Abbreviation | Definition |
| --- | --- |
| AE | adverse event |
| AIS | acute ischemic stroke |
| aICH | asymptomatic intracranial hemorrhage |
| AUC | area under the concentration-time curve |
| aPTT | activated partial thromboplastin time |
| BID | "bis in die", twice a day |
| ECG | electrocardiogram |
| $C_{max}$ | maximum plasma concentration |
| $C_{trough}$ | pre-dose trough concentration |
| CDER | Center for Drug Evaluation and Research |
| CT | computed tomography |
| CTA | computed tomography angiography |
| CCA | common carotid artery |
| CL | total body clearance of the drug from plasma |
| ECA | external carotid artery |
| EVT | endovascular thrombectomy |
| HE | hematoxylin and eosin |
| HED | human equivalent dose |
| ICA | internal carotid artery |
| IV | Intravenous |
| mRS | modified Rankin Scale |
| mTICI | modified Treatment in Cerebral Infarction |
| MRSD | Maximum recommended starting dose |
| MRI/CTP | magnetic resonance imaging or computed tomography perfusion |
| MRA | magnetic resonance angiography |
| MCAO | Middle Cerebral Artery Occlusion |
| MoCA | Montreal Cognitive Assessment |
| NIHSS | National Institute of Health Stroke Scale |
| NOAEL | no observed adverse effect levels |
| NSS | neurological severity score |
| NDS | neurological deficit scores |
| PK | pharmacokinetic |
| PPA | pterygopalatine artery |
| PT | prothrombin time |
| rtPA | recombinant tissue-type plasminogen activator |
| RT | room temperature |
| RBC | red blood cell |
| RP2D | recommended phase II dose |
| rCBF | regional cerebral flow |
| SAE | serious adverse event |
| SBP/DBP | systolic and diastolic blood pressure |
| SD rat | Sprague-Dawley rat |
| sICH | symptomatic intracranial hemorrhage |
| PIT | photochemically induced thrombotic |
| $T_{1/2}$ | elimination half-life |
| TEAE | treatment emergent adverse events |
| $T_{max}$ | time to reach maximum plasma concentration |
| TID | "ter in die", three times a day |
| TT | thrombin time |
| TTC | 2,3,5-triphenyltetrazolium chloride |
| $V_{SS}$ | volume of distribution at steady state |

Example 1. Embolic Stroke Model in SD Rat

A 10% chloral hydrate solution (400 mg/kg) was injected intraperitoneally into SD male rats (240-320 g) for anesthesia. A vertical incision of about 2 cm in length was made on the right side near the center of the neck, and the right common carotid artery (CCA), external carotid artery (ECA) and internal carotid artery (ICA) were separated along the margin of the inner side of sternocleidomastoid muscles. The incision at the internal carotid artery and the proximal end of the common carotid artery were clipped respectively with noninvasive arterial clips. A small incision was made on the external carotid artery, and the distal end of the external carotid artery was ligated. The arterial clip at the proximal end of the common carotid artery was released, and 10 µl blood was drawn. After blood was drawn, the proximal end of the common carotid artery was again clipped with a noninvasive arterial clip. The 10 µl blood drawn was placed in a 1 mL EP vial and kept at RT for 30 min to allow the coagulation of blood and then transferred into a −20° C. refrigerator for 1 hour to allow the formation of solid coagulation. 1 hour later, the blood clots were taken out, 1 mL normal saline was added therein, and then the blood clots were broken into relatively uniform microthrombus by a steel spatula. The microthrombus suspension was then transferred into a 1 mL injector for use. When the clip on the internal carotid artery of the rat was released, the 1 mL thrombus suspension in the injector was slowly injected from the external carotid artery of the rat to its proximal end, and then was injected into the brain of the rat through the internal carotid artery. Subsequently, the proximal end of the external carotid artery was ligated, the arterial clips on the internal carotid artery and the common carotid artery were released, and blood flow was restored. The common jugular vein was separated, and then injected with normal saline solution, or tested compound. The vein was ligated. 3 drops of penicillin was dropped on the wound. The wound was sewed, and animals were waited for awake.

24 hours after the rats were awake, the degree of damage in neural function was evaluated by the Zealonga method. A score of 0 indicated no sign of loss in neural function, 1 indicated the front limbs on the undamaged side could not stretch out, 2 indicated walking toward the undamaged side, 3 indicated tail-chasing walking in circles toward the undamaged side, 4 indicated involuntary walking with disturbance of consciousness, and 5 indicated death. The evaluation results were statistically analyzed and subjected to t-test.

After the rats were awake for 24 hours and assessed for their degree of damage in neural function by Zealonga method, they were anesthetized with urethane followed by immediate decapitation and removal of the brain. Brain tissues were kept in a −20° C. refrigerator for 2 hours, and coronal sections of about 2 mm were successively sliced from the prefrontal end for a total of 5 sections and then placed into a 2% TTC solution to incubate without light at 37° C. for 30 min. The color change in brain sections was observed: normal brain tissues were stained red by TTC, while ischemic brain tissues appeared in white. Photographs were taken by using a digital camera and processed with image statistics software, and the volume of infarction in brain tissues and the area of normal brain tissues in the coronal sections were calculated. The ratio of the cerebral infarction volume of each group was statistically calculated and subject to t-test.

Example 2. Middle Cerebral Artery Occlusion (MCAO) Model

MCAO Surgery in Wistar Rat

At Day 0, anesthetize the rats to collect blood from the femoral artery to prepare the homologous clot. Create a partial arteriotomy with a microscissors and then insert a sterile PE-50 tubing (40-50 mm) along the artery. Arterial blood collected in this length of the PE-50 tubing commonly generates ~10 indusial clots that are suitable for MCAO. Keep the clot in the tube for 2 hours at room temperature and subsequently retain for 22 hours at 4° C.

At Day 1, to prepare the embolus, cut the clot containing PE-50 tubing into 32 mm segment in length and connect the segment with a 3 ml saline filled syringe with 23G needle. Push the syringe to flush the clot out of the PE-50 tubing into saline filled Petri dish. Draw and flush the clot into and out of the PE-10 tubing (draw from clot's end to avoid folding and twisting of the clot), respectively, 10-15 times to wash out the majority of the entrapped red blood cells until the clot without further RBCs releasing. Connect the PE-10 tubing to the modified PE-50 catheter and shift the clot into PE-50 catheter. Then, the modified PE-50 catheter is connected to a 100 µl Hamilton microsyringe. The clot is now ready to be used.

At Day 1, anesthetize the rats. Bluntly dissect the carotid sheath along the common carotid artery (CCA) until the ECA (ipsilateral external carotid artery), PPA (pterygopalatine artery), and ICA (internal carotid artery) bifurcation is exposed. Dissect the occipital artery and the superior thyroid artery (the first and second branches of ECA) and use bipolar micro coagulator to remove the vessel from ECA. Prepare laser Doppler flow probe into the tube of head. Temporarily clamp the CCA, PPA, and ICA with clip and apply a 4-0 silk suture loosely around the trunk of the ECA near bifurcation. Release the clip slowly and further advance the catheter within the ICA to enter the intracranial segment of the ICA until resistance is felt. The total length of the catheter that has been advanced is −19-22 mm from the ECA arteriotomy site. Retract the catheter 1-2 mm and slowly inject the clot with 5-10 µl of saline at rate of 10 µl/min. The percentage of regional cerebral flow (rCBF) decrease into ~20-30% after clot injection. Wait for 30 minutes to let the clot stable at the ICA. Retract the catheter until its tip reaches the ECA/ICA bifurcation. Re-apply a clip to temporarily clamp the CCA and the ICA and then withdraw the catheter from the arteriotomy. Tighten the 4-0 silk suture around the ECA trunk to ligate the arteriotomy. Remove the clip. Wait for another 30 minutes to make sure the animal is stable and there is no blooding issue. Close the incision and terminate the anesthesia.

Neurological Function Test

Neurological deficits were assessed at 24 h after MCAO surgery. The neurological function was graded on a scale of 0-18, with 0 representing normal function and 18 representing maximum neurological deficits (see FIG. 2).

TTC Staining and Infarct Size and Swelling Ratio Calculation 24 hours after the induction of MCAO, anesthetize the rat with 5% isoflurane and use normal saline to do the perfusion from heart (150 ml). Decapitate the rat and collect the brain. Rinse the collected dish and matrix with PBS before used. To tear out clot after taking photo. Slice the brain coronally into four 2-mm slices with a brain matrix on ice (Cut the brain into 8 pieces). Incubate the brain slices in 2% 2,3,5-triphenyltetrazolium chloride (TTC) (Sigma-Aldrich) in 1×PBS for 20 min at room temperature (avoid light) and record the result by photo. Then, using ImageJ to determine the size and extent of the infarction.

The caudal sides of all the TTC sections were scanned using a digital camera, and the images were stored as JPEG. The non-ischemic and ischemic hemisphere infarct areas were measured using image J (Image J, Bethesda, MD) software. All eight infarct area measurements were calculated with a 2 mm distance between the slices. Using these measurements, the total infarct size (%) was calculated for each brain.

Infarct size (%) calculation of each section: 100*[(volume of healthy hemisphere−volume of nonlesioned ipsilateral hemisphere)/volume of healthy hemisphere]

Total infarct size (%): Sum of eight sections/8

Brain swelling ratio (%) calculation of each section: 100*[(volume of infarcted hemisphere−volume of healthy hemisphere)/volume of healthy hemisphere]

Total swelling ratio (%): Sum of eight sections/8

Measurement of Cerebral Blood Flow (rCBF)

To measure the rCBF, dissect the temporal muscle from the bone. (At this time, bleeding from the skin and muscle must be controlled with bipolar coagulator, especially in the case of using rtPA). Thin the bone at 2 mm posterior and 6 mm lateral to the bregma by drilling. Place the laser Doppler flow probe with superglue and start monitoring regional cerebral blood flow (rCBF).

Example 3. Photochemically Induced Thrombotic (PIT) Stroke Model

Photochemically-Induced Thrombosis of the Middle Cerebral Artery

Under anesthesia, the left middle cerebral artery (MCA) was occluded by a thrombus generated at the site of photoirradiation. The left MCA was exposed via a transorbital approach. A vertical incision was made between the left orbital and the external auditory canal. The temporal muscle was reflected and a subtemporal craniotomy was performed without removing the zygomatic arch. A window of approximately 3 mm in diameter was opened at the base of the skull. The main trunk of the left MCA was visible through the window. Endothelial cells in the MCA were focally injured by a photochemical reaction between rose bengal and green illumination (X540 nm, 600,000 Lux). Rose bengal (20 mg/kg) was intravenously dose and then the MCA was exposed to green light for a period of 10 min. During surgery, animals were placed on a heating pad set at 38 C.

Rat Neurologic Deficits Score Evaluation

Twenty-four hours (±2 hrs.) after thromboembolism, and once daily for the next five days, neurologic deficits were scored according to a modified method described by Ederson et al. (Stroke, 1986, 17: 472-476). A total of "0" indicates no deficit whereas a maximal score of "15" indicates severe deficits.

1) Forelimb Flexion

Rats were held gently by the tail, suspended about 10 cm above the floor, and observed for forelimb flexion
0: Both forelimbs toward the floor
1: Slight difference between forelimb extension
2: Mild wrist flexion and shoulder adduction with extension at the elbow
3: Severe posturing with full flexion of the wrist, elbow and adduction with internal rotation of the shoulder 2) Hindlimb Flexion With the rat at rest, the hindlimbs, with the soles facing up, were gently pulled toward the tail.
0: Retraction response is not different between hindlimbs
1: Retraction response of the right hindlimb is weaker than that of the left hindlimb
2: Right hindlimb is extended abnormally, but retractable when the sole is touched with a finger
3: Right hindlimb is extended abnormally, and is not retractable when the sole is touched with a finger 3) Rotational Behavior Rats were held gently by the tail, and with their forelimbs on the floor, circling behavior was observed.
0: Walks forward
1: Usually walks forward, and cannot walk towards the left
2: Usually walks toward the right, and can walk ahead
3: Walks towards the right, and cannot walk forward.

4) Lateral displacement

With the rat at rest, gentle lateral pressure was applied behind the rat's shoulder from either direction.
0: Resists sliding equally in either direction
1: Resistance to a lateral push towards the right is slightly reduced
2: Resistance to a lateral push toward the right is marked reduced
3: Resistance to a lateral push towards the right is markedly reduced and the rat falls on its back 5) General Posture With the rat at rest, general posture was observed.
0: General posture after surgery is not different from that of normal rats
1: When looking at the rats from above, the left forelimb and hindlimb can be seen
2: Body leans slightly
3: Marked body leaning Brains for Hematoxylin and Eosin Staining Each brain was cut into six coronal blocks with a rat brain matrix (2 mm interval). Brains were post-fixed overnight in 4% paraformaldehyde at 3.1-6.2° C., stored in phosphate-buffered saline and sent out for histological processing. Each coronal block was embedded in paraffin. One coronal section from each block was taken and stained with hematoxylin and eosin (HE).

From the HE-stained sections, the infarct areas ($mm^2$) were manually marked using OsiriX version 8.0.2 (Pixmeo SARL, Bernex, Switzerland). The volume of ischemic infarction ($mm^3$) was calculated as the sum of the infarct area of each coronal section (six coronal sections per brain). Infarct volumes were calculated in cerebral cortex and basal ganglia. Total infarct volume was calculated by adding the infarct volumes of the basal ganglia and cerebral cortex.

Example 4. Preclinical Efficacy of Single Dose of DC009 in Rat Embolic Stroke Model (Treatment Time Window at 3 Hours Post Stroke)

The purpose of this study was to evaluate the efficacy of single administration of DC009 at 0.007 mg/kg at 3 hours after stroke onset in embolic stroke model in Sprague-Dawley rats as described in Example 1.

An embolic occlusion of the middle cerebral artery in male Sprague-Dawley rats was induced by introducing blood clots into the carotid artery. Rats were treated with vehicle (saline), rtPA (10 mg/kg, IV bolus injection), or DC009 (0.007 mg/kg, IV bolus injection) after 3 hours of stroke onset (n=12-13 per treatment group). At 24 hours after drug administration, rats were assessed with a neurological deficit scale (NDS) (0=no sign of loss of neural function, 1=left front limbs could not stretch out, 2=walking toward the left side, 3=tail-chasing walking in circles toward the left side, 4=involuntary walking with disturbance of consciousness, 5=death). After the neurological evaluation, animals were sacrificed and coronal brain sections (2 mm thick) were stained with TTC. Infarct volumes were quantified using computer-assisted image analysis techniques.

The NDS and infarct volume of rats at 24 hours after stroke are summarize in the following Table 1.

TABLE 1

| Group | Treatment | Mean neurological deficit scores (NDS) | infarct volumes (% hemisphere) |
|---|---|---|---|
| Saline | 0.9% NaCl | 3.00 ± 1.60 | 14.07 ± 12.04% |
| DC009 | 0.007 mg/kg | 1.54 ± 1.20* | 8.39 ± 7.95% |
| rtPA | 10 mg/kg | 2.13 ± 1.173 | 12.74 ± 9.02% |

*P ≤ 0.05 vs saline

The DC009-treated group (0.007 mg/kg) showed improved neurological behavior score and reduced brain infarct volume versus saline treated groups. Therefore, DC009 drug product, administered as an IV bolus injection at 0.007 mg/kg at 3 hours post-stroke was efficacious in a preclinical rat embolic stroke model.

Example 5. Preclinical Efficacy of Single Dose of DC009 in Rat Embolic Stroke Model (Treatment Time Window at 6 Hours Post Stroke)

The objective of this study was to evaluate the efficacy of a single administration of 0.007 mg/kg DC009 given 6 hours after stroke onset in an embolic stroke model in male Sprague-Dawley (SD) rats as described in Example 1.

An embolic occlusion of the middle cerebral artery in male SD rats was induced by introducing a blood clot into carotid artery. Blood clots, made by homologous whole blood, were slowly injected in the external carotid artery of the rat to its proximal end, and then infused through the internal carotid artery. Rats were treated with vehicle (saline), rtPA (3 mg/kg, intravenous bolus injection), or DC009 (0.007 mg/kg, intravenous bolus injection) given 6 hours after of stroke onset (n=11-12 per treatment group). At 24 hours after drug administration, rats were assessed with a 6-point neurological deficit scale. After the neurological evaluation, animals were sacrificed and coronal brain sections (2 mm thick) were stained with TTC. Infarct volumes were quantified using computer-assisted image analysis techniques.

The NDS and infarct volume of rats at 24 hours after stroke are summarize in the following Table 2.

TABLE 2

| Group | Treatment | Mean neurological deficit scores (NDS) | infarct volumes (% hemisphere) |
|---|---|---|---|
| Saline | 0.9% NaCl | 2.25 ± 0.97 | 20.13 ± 12.31% |
| DC009 | 0.007 mg/kg | 1.67 ± 1.37* | 8.68 ± 5.93%* |
| rtPA | 3 mg/kg | 3.27 ± 1.85 | 17.90 ± 7.47% |

*P ≤ 0.05 vs saline

The DC009 treated group (0.007 mg/kg) showed improved neurological behavior scores and reduced brain infarct volume versus the saline treated groups. Therefore, DC009 drug product, administered as a single intravenous bolus injection (0.007 mg/kg) at 6 hours post stroke, was efficacious in the preclinical rat embolic stroke model.

Example 6. Preclinical Efficacy of Multiple Dose of DC009 in Rat Embolic Stroke Model (Treatment Time Window at 24 Hours Post Stroke, QD6)

The objective of this study was to evaluate the efficacy of repeat administration of DC009 for 6 consecutive days at doses of 0.0007 mg/kg, 0.007 mg/kg, and 0.07 mg/kg in an embolic stroke model in rats as described in Example 1.

An embolic occlusion of the middle cerebral artery in male Sprague-Dawley rats was induced by introducing blood clot into the carotid artery. Rats were treated with either vehicle (saline) or DC009 (0.0007 mg/kg, 0.007 mg/kg, and 0.07 mg/kg, intravenous bolus injection) after 24 hours of stroke onset and once daily for additional 5 days (n=9-10 per treatment group). At 24 hours after drug administration and once daily before the drug administration, rats were assessed with a neurological deficit scale. After the last neurological evaluation, animals were sacrificed, and coronal brain sections (2 mm thick) were stained with TTC. Infarct volumes were quantified using computer-assisted image analysis techniques.

The infarct volume of rats at 7 days after stroke are summarize in the following Table 3.

TABLE 3

| Group | Treatment | infarct volumes (% hemisphere) |
|---|---|---|
| Saline | 0.9% NaCl | 16.61 ± 10.94% |
| DC009 | 0.0007 mg/kg | 9.95 ± 10.32% |
| DC009 | 0.007 mg/kg | 5.23 ± 7.72%* |
| DC009 | 0.07 mg/kg | 5.73 ± 3.24* |

*P ≤ 0.05 vs saline

Although neurological outcomes were also assessed, the interpretation of the data is confounded by the differences in baseline scores across treatment groups (data not shown). To conclude, repeat IV bolus administration of DC009 for 6 consecutive days at 0.007 mg/kg and 0.07 mg/kg was efficacious in a preclinical rat embolic stroke model.

Data from Example 4-6 showed that the effective dose in the rat Embolic Stroke Model of Example 1 for DC009 treatment is 0.007-0.07 mg/kg. The therapeutic efficacy is also demonstrated at 24 hours after stroke, which indicate the potency has good prospects for clinical application.

Example 7. Preclinical Efficacy of Single Dose of DC009 in Rat MCAO Model (Treatment Time Window at 3 Hours Post Stroke, SD)

The objective of this study was to assess the therapeutic efficacy of a single administration of 0.05 mg/kg and 0.005 mg/kg DC009 in embolic middle cerebral artery occlusion (MCAO) rats as described in Example 2.

An embolic occlusion of the middle cerebral artery in male Wistar rats was induced by introducing a blood clot into the carotid artery. Blood clots, made by homologous whole blood, were slowly injected in the internal carotid artery. Rats were treated with either vehicle (saline) or rtPA (10 mg/kg, initial 10% intravenous bolus followed by infusion of the remaining drug for 30 minutes), or DC009 (0.05 or 0.005 mg/kg) via 15-minute IV infusion 3 hours after stroke onset (n=8-9 per treatment group). Neurological deficits were evaluated prior to treatment, 3 hours post-MCAO surgery and 24 hours post-MCAO surgery. The neurological severity score (NSS) was graded on a scale of 0-18, with 0 representing normal and 18 representing severe impairment. Animals with an NSS of >7 three hours post-surgery were placed in one of the treatment groups. The neurological function of treated animals was then assessed 24 hours post-surgery. After neurological evaluation, animals were euthanized, and brains were stained with 2% 2,3,5-triphenyltetrazolium chloride (TTC) solution to quantify infarct size. Image J software was used to calculate the percentage of ischemia and brain swelling ratio.

TABLE 4

| Group | Treatment | Mean neurological severity score (NSS) | infarct volumes (% hemisphere) |
|---|---|---|---|
| Saline | 0.9% NaCl | 7.22 ± 1.09 | 49.29 ± 10.73 |
| DC009 | 0.005 mg/kg | 7.13 ± 0.64 | 31.95 ± 10.53* |
| DC009 | 0.05 mg/kg | 6 ± 0.76* | 23.53 ± 13.75*** [a] |
| rtPA | 10 mg/kg | 6.38 ± 0.74 | 43.23 ± 11.03 |

*p < 0.05 versus saline;
***p < 0.001 versus saline,
[a] p < 0.01 verse rtPA

In MCAO model, at 24 hours post-stroke, the NSS after DC009 treatment at dose level of 0.05 mg/kg was significantly lower than saline treatment. DC009 at dose level of 0.005 mg/kg and 0.05 mg/kg also reduced infarct size significantly when compared to rtPA and saline treatment (Table 4).

Example 8. Preclinical Efficacy of Single Dose of DC009 in Rat MCAO Model (Treatment Time Window at 1 Hours Post Stroke, SD)

The objective of this study was to assess the therapeutic efficacy of a single administration of 0.05 mg/kg, 0.1 mg/kg, 0.2 mg/kg and 0.4 mg/kg DC009 in embolic middle cerebral artery occlusion (MCAO) rats as described in Example 2.

An embolic occlusion of the middle cerebral artery in male Wistar rats was induced by introducing a blood clot into the carotid artery. Blood clots, made by homologous whole blood, were slowly injected in the internal carotid artery. Rats were treated with either vehicle (saline) or rtPA (10 mg/kg, initial 10% intravenous bolus followed by infusion of the remaining drug for 30 minutes), or DC009 (0.05 mg/kg, 0.1 mg/kg/, 0.2 mg/kg and 0.4 mg/kg) via 15-minute IV infusion 1 hours after stroke onset (n=5-8 per treatment group). Blood flow were measured for 3 hours.

In FIG. 3, data showed that blood flow was increased in rtPA and all DC009 treated group compared to saline treated group (p<0.0001 vs saline). DC009 at a low dose of 0.05 mg/kg dose demonstrated good efficacy in restoring occluded blood flow in rats.

Example 9. Preclinical Efficacy of Multiple Dose of DC009 in Rat MCAO Model (Treatment Time Window at 3 Hours Post Stroke, Twice a Day)

The purpose of this study was to assess the therapeutic efficacy of twice a day administration of DC009 for one day in embolic MACO rats as described in Example 2.

Figure 4:
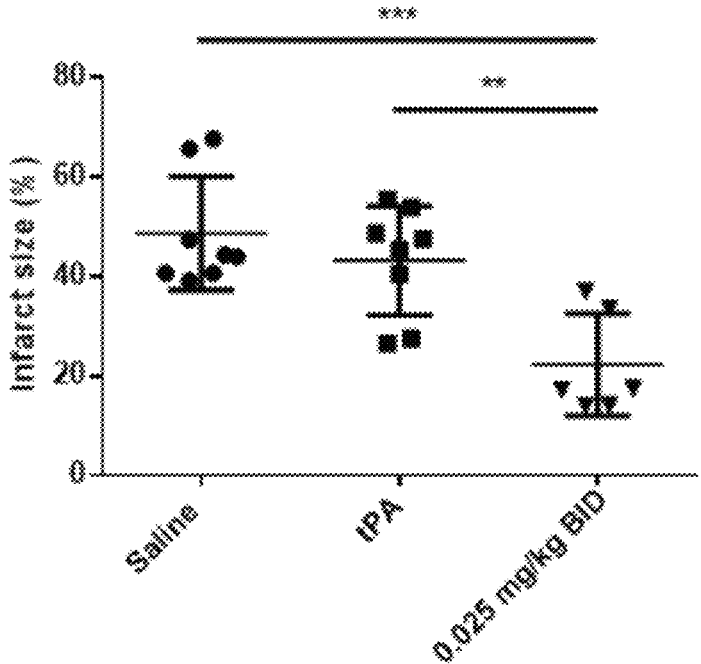
FIG. 4 shows the infarct size result for multiple doses of DC009 in rat MCAO model.

A total of 22 rats were received saline (n=8), 10 mg/kg rtPA (n=8) treatment at 3 hours post MCAO surgery, and 0.025 mg/kg DC009 (n=6) treatment at 3 and 6 hours post MCAO surgery. All animals were sacrificed at 24 hours after stroke and the brain tissues were cut into eight pieces using brain slicer matrix. The sections were further stained with 2% 2,3,5-triphenyltetrazolium chloride (TTC) solution and used Image J software to calculate the percentage of ischemia region and brain swelling ratio. The result indicated that twice administration of DC009 for one day resulted in the significant smaller infarct size when compared to saline and rtPA treated groups (FIG. 4).

Example 10. Preclinical Efficacy of Single Dose of DC009 in Rat Photochemically Induced Thrombotic Stroke Model (Treatment Time Window at 1 Hour and 3 Hours Post Stroke)

The objective of this study was to evaluate the efficacy of administration of DC009 once a day at 0.007 mg/kg in a photochemically induced thrombotic (PIT) stroke model in rats as described in Example 3.

Rats were treated with vehicle (saline), rtPA (10 mg/kg), DC009 (0.007 mg/kg, 15-minute IV infusion) after 1 hours of stroke onset, or DC009 (0.007 mg/kg, 15-minute IV infusion) after 3 hours of stroke onset. (n=10 per treatment group). At 24 hours after drug administration, rats were assessed with a neurological deficit scale (NDS).

24 hours after PIT surgery, rats were euthanized, and brains were processed for TTC staining. The infarction volume is summarized in the following Table 5.

TABLE 5

| Group | Treatment | Time | Basal ganglia | Cerebral cortex | Total |
|---|---|---|---|---|---|
| vehicle | 0.9% NaCl | | 97.8 ± 7.3 | 267.5 ± 20.0 | 365.3 ± 25.0 |
| rtPA | 10 mg/kg | 1 hr post-PIT | 80.7 ± 4.3 | 200.0 ± 18.1 | 280.7 ± 20 |
| rtPA | 10 mg/kg | 3 hr post-PIT | 87.0 ± 7.0 | 173.5 ± 19.4 ** | 260.6 ± 23.9 ** |
| DC009 | 0.007 mg/kg | 1 hr post-PIT | 63.7 ± 10.3 ** | 210.6 ± 26.4 | 274.4 ± 33.2 * |
| DC009 | 0.007 mg/kg | 3 hr post-PIT | 94.8 ± 6.2 | 227.7 ± 18.4 | 322.5 ± 23.0 |

* P < 0.05 vs. vehicle ;
** P < 0.01 vs. vehicle

Compared to vehicle treatment, either DC009 or rtPA reduced infarction, at a different time of administration following PIT surgery. Early rtPA treatment (one hour after PIT surgery) reduced total brain infarction volume compared to vehicle treatment. DC009 treatment one hour after PIT surgery also significantly reduced total brain infarction, compared to vehicle treatment.

Example 11. Study 101: Safety, Tolerability, and Pharmacokinetics of DC009 Drug Product in Healthy Volunteers The primary objective of this Phase 1, double-blind, randomized, placebo-controlled study was to determine the safety, tolerability, and pharmacokinetics of single ascending doses of DC009 drug product administered by 15-minute IV infusion in healthy subjects. The secondary objectives were to characterize the pharmacodynamics of single-ascending doses, explore the pharmacokinetic-pharmacodynamic relationships of single-ascending doses, and to determine the RP2D of the DC009 drug product.

The subject population was healthy adult male and female subjects between the ages of 18 and 65 years. Sixteen healthy subjects completed the study. All subjects received a single dose of DC009 drug product or placebo administered via a 15-minute IV infusion.

Cohort 1 (8 subjects) was administered 0.05 mg/kg DC009 drug product or placebo, and Cohort 0 (8 subjects) was administered 0.025 mg/kg DC009 drug product or placebo. The dosage and design is summarized in Table 6.

TABLE 6

| Cohort | Dose Level (mg/kg) | Subject No. for DC009 drug product | Subject No. for Placebo | Administration time |
|---|---|---|---|---|
| 0 | 0.025 mg/kg | 6 | 2 | 15-minute IV infusion |
| 1 | 0.05 mg/kg | 6 | 2 | 15-minute IV infusion |

Primary Endpoints:

Nature and severity of adverse events (AEs) and number of subjects with AEs

Changes from baseline in vital signs, electrocardiogram (ECG) results, laboratory abnormalities, plasmin-anti-plasmin complex, euglobulin clot lysis time, platelet aggregation, and physical examination findings Pharmacokinetic parameters: maximum plasma concentration ($C_{max}$), time to reach the observed maximum (peak) concentration ($T_{max}$), area under the plasma concentration-time curve from time zero to the time of the last quantifiable concentration ($AUC_{0-t}$), area under the plasma concentration-time curve from time zero to the time of the last quantifiable concentration ($AUC_{0-t}$), elimination half-life ($T_{1/2}$), total body clearance of the drug from plasma (CL), and volume of distribution Secondary Endpoints Pharmacodynamic effects of DC009 drug product on blood pressure, thrombin time (TT), prothrombin time (PT), euglobulin clot lysis time, and activated partial thromboplastin time (aPTT) up to 48 hours after dosing Relationship between DC009 plasma concentrations and the selected PD and safety parameters RP2D (recommended phase II dose)

Results

The DC009 drug product was safe and well-tolerated in both dosing cohorts. There were no serious adverse events (SAEs) reported in either cohort. There were no AEs reported in Cohort 0. In Cohort 1, TEAEs were reported by 2 subjects in the 0.05 mg/kg dose group (headache, contact dermatitis) and in 1 subject receiving placebo (injection site hematoma).

Safety data collected in this study also included vital signs (heart rate, blood pressure, respiratory rate, and body temperature), ECGs, clinical chemistry, urinalysis, hematology, coagulation parameters, and stool occult blood test. There were no clinically significant findings in any of the safety parameters measured.

The pharmacokinetic parameters of DC009 drug product were assessed included maximum plasma concentration ($C_{max}$), time to reach $C_{max}$ ($T_{max}$), area under the plasma concentration-time curve from time zero to infinity ($AUC_{0-\infty}$), area under the plasma concentration-time curve from time zero to the time of the last quantifiable concentration ($AUC_{0-t}$), elimination half-life ($T_{1/2}$), total body clearance of the drug from plasma (CL), and volume of distribution at steady state ($V_{ss}$). A single sample of blood was collected at the following time points for the quantification of DC009 in plasma: at predose, 5, 10, 15 (end of infusion), 20, 25, 30, and 45 minutes; and at 1, 2, 4, 6, 12, 18, and 24 hours after infusion was initiated.

The data from Table 8 show that DC009 is rapidly cleared from the systemic circulation, only measurable within the first half-hour in the plasma samples after the start of the infusion. The mean of $T_{1/2}$ was 0.054 hours, ranged between 0.05 and 0.07 hours. $T_{max}$ occurred between 6 and 18 minutes. Volume of distribution and clearance were higher following the 0.05 mg/kg dose compared with the 0.025 mg/kg dose. Data suggested that DC009 exposure from the DC009 drug product is approximately dose proportional. AUC and $C_{max}$ following the 0.05 mg/kg dose were slightly less than twice that following the 0.025 mg/kg dose. The dose-normalized geometric mean ratio of the 0.025 mg/kg dose to the 0.05 mg/kg dose was 1.40 for $AUC_{0-inf}$ and 1.46 for $C_{max}$.

Data show that the mean $C_{max}$ of 0.05 mg/kg and 0.025 mg/kg were both lower than the safe 110 ng/mL plasma exposure limit of DC009. Results from Subject 001-008 ($C_{max}$ of 152 ng/mL) and Subject 001-042 ($C_{max}$ of 120 ng/mL) indicate that DC009 was tolerable in human with a $C_{max}$ at about 150 ng/mL.

TABLE 7

| Subject ID | $AUC_{0-t}$ (ng * hr/mL) | $C_{max}$ (ng/mL) | Elimination Half-life (min) |
|---|---|---|---|
| | Cohort 1, 0.05 mg/kg | | |
| 001-084 | 4.62 | 24.7 | N/A |
| 001-008 | 31.86 | 152 | N/A |
| 001-029 | 19.18 | 65.7 | 4.2 |
| 001-045 | 19.84 | 87.8 | N/A |
| 001-042 | 26.42 | 120 | 3.0 |
| 001-070 | 23.80 | 94.9 | 3.6 |
| Mean ± SEM | 21.0 ± 3.8 | 90.9 ± 17.9 | 3.60 ± 0.2 |
| | Cohort 0, 0.025 mg/kg | | |
| 001-142 | 15.23 | 65.1 | N/A |
| 001-156 | 10.07 | 57.5 | N/A |
| 001-153 | 12.05 | 51.6 | N/A |
| 001-155 | 16.06 | 68.7 | 3.0 |
| 001-150 | 11.18 | 42.5 | 3.6 |
| 001-145 | 14.83 | 73.8 | N/A |
| Mean ± SEM | 13.2 ± 1.0 | 59.9 ± 4.7 | 3.30 ± 0.2 |

Example 12. Study 103: Safety, Tolerability, and Pharmacokinetics of DC009 Drug Product in Healthy Volunteers The objective of this phase I, double-blind, randomized, placebo-controlled study was to evaluate the safety, tolerability, and pharmacokinetics of multiple doses of DC009 drug product in healthy adult subjects.

TABLE 8

| Dose Level | Subject No. for DC009 drug product | Subject No. for Placebo | Administration time |
|---|---|---|---|
| 0.025 mg/kg | 10 | 2 | 15-minute IV infusion, BID Q12 h, 3 days (*) |
| 0.05 mg/kg | 11 | 1 | 30-minute IV infusion, BID, Q12 h, 3 days (*) |

* twice a day the 2nd dose is supposed to be taken 12 hours after the time of the first dose Primary Endpoints:

Nature and severity of AEs and number of subjects with AEs

Changes from baseline in vital signs, electrocardiogram (ECG) results, laboratory abnormalities and physical examination findings Pharmacokinetic parameters: maximum plasma concentration ($C_{max}$), time to reach the observed maximum (peak) concentration ($T_{max}$), area under the plasma concentration-time curve from time zero to infinity ($AUC_{0-\infty}$), area under the plasma concentration-time curve from time zero to the time of the last quantifiable concentration ($AUC_{0-t}$), elimination half-life ($T_{1/2}$), total body clearance of the drug from plasma (CL), and volume of distribution.

Secondary Endpoints

Pharmacodynamic effects of DC009 drug product on blood pressure, prothrombin time (PT), and activated partial thromboplastin time (aPTT) up to 24 hours after dosing Results The pharmacokinetic parameters of DC009 drug product were assessed included maximum plasma concentration ($C_{max}$), time to reach $C_{max}$ ($T_{max}$), area under the plasma concentration-time curve from time zero to infinity ($AUC_{0-\infty}$), area under the plasma concentration-time curve from time zero to the time of the last quantifiable concentration ($AUC_{0-t}$), elimination half-life ($T_{1/2}$), total body clearance of the drug from plasma (CL), and volume of distribution at steady state ($V_{ss}$). For 0.025 mg/kg group, a single sample of blood after the $1^{st}$ dosing (day 1) and the $5^{th}$ dosing (day 3) was collected at the following time points for the quantification of DC009 in plasma: at predose, 5, 10, 15 (end of infusion), 20, 25, 30, 45 and 60 minutes. For 0.05 mg/kg group, a single sample of blood after the $1^{st}$ dosing (day 1) and the $5^{th}$ dosing (day 3) was collected at the following time points for the quantification of DC009 in plasma: at predose, 10, 20, 30 (end of infusion), 35, 40, 45 50, 60 and 70 minutes.

TABLE 9

| Group | $AUC_{0-t}$ (ng * hr/mL) Mean ± SD | $C_{max}$ (ng/ml) Mean ± SD | Maxima $C_{max}$ (ng/mL) | Elimination Half-life (min) Mean ± SD |
|---|---|---|---|---|
| 0.025 mg/kg 15-min infusion $1^{st}$ dosing | 13.32 ± 2.94 | 56.28 ± 12.54 | 78.7 | 2.84 ± 0.71 |
| 0.025 mg/kg, 15-min infusion $5^{th}$ dosing | 13.54 ± 3.40 | 56.84 ± 14.52 | 72.6 | 2.61 ± 0.44 |
| 0.05 mg/kg 30-min infusion $1^{st}$ dosing | 21.96 ± 4.75 | 50.16 ± 11.39 | 75.2 | 3.67 ± 1.31 |
| 0.05 mg/kg 30-min infusion $5^{th}$ dosing | 24.74 ± 4.51 | 57.32 ± 11.01 | 72.5 | 5.47 ± 3.58 |

The DC009 drug product was safe and well-tolerated in 0.025 mg/kg (15-minute infusion) and 0.05 mg/kg (30-minute infusion) in human subjects when administrated in the subject twice a day for 3 days. The levels of reported AEs are all defined as grade I and considered to be unrelated or unlikely related. The safety risk is well-controlled.

The $T_{max}$ and $C_{max}$ after single and multiple administration of 0.025 mg/kg (15-minuets infusion) and 0.05 mg/kg (30-minutes infusion) were similar. The $AUC_{0-t}$, $AUC_{0-\infty}$ of 0.05 mg/kg was higher than 0.025 mg/kg group. The $C_{max}$ of both group all under the 110 ng/mL exposure limit.

No significant effect of blood pressure (SBP/DBP) and coagulation factor (PT/APTT) was observed after 0.025 mg/kg and 0.05 mg/kg administration.

Based on the safety results of the healthy volunteers of the trial, the 3-day intravenous infusion of multiple doses of DC009 drug product was safe and well-tolerated in healthy volunteers, and the $C_{max}$ is far below the exposure limit.

Example 13. Study 105: Safety, Tolerability, and Pharmacokinetics of DC009 Drug Product in Healthy Volunteers The objective of a double-blind, randomized, placebo-controlled, phase 1 study is to evaluate the safety, tolerability, and pharmacokinetics of multiple doses of DC009 drug product and drug-drug interaction in healthy adult subjects.

Part A

To determine the safety, tolerability, and PK of a 3-day thrice daily (TID) use of DC009 drug product, when administered as an IV infusion Q3h between each dose within one day in healthy subjects. Part A is double-blind, placebo-controlled study, this study will examine the safety and PK profiles of multiple doses of DC009 drug product in healthy subject.

TABLE 10

| Dose Level (mg/kg) | Subject No. for DC009 drug product | Subject No. for Placebo | Administration time |
|---|---|---|---|
| 0.025 mg/kg | 12 | 4 | 15-minute IV infusion, TID, Q3 h, 3 days |

* three times a day, the 2nd dose is supposed to be taken 3 hours after the time of the first dose and the 3rd dose is supposed to be taken 3 hours after the time of the 2nd dose Endpoints Nature and severity of AEs and number of subjects with AEs Changes from baseline in physical examination, vital signs, ECG assessment, oximetry, coagulation, and clinical laboratory tests.

Plasma and urine PK parameters

Effect on systolic and diastolic blood pressure (SBP/DBP), prothrombin time (PT), activated partial thromboplastin time (aPTT), and thrombin time (TT).

Part B

An open-label study to assess the safety and PK of DC009 when co-administered with aspirin, clopidogrel, apixaban or dabigatran.

TABLE 11

| Group | DC009 Administration time | Drug Dose Level | Subject No. |
|---|---|---|---|
| aspirin | Day 1: a single 15-minute IV infusion of 0.025 mg/kg Day 6-8: 15-minute IV infusion of 0.025 mg/kg, TID, Q3 h* | Day 2: 325 mg aspirin Day 3-8: 81 mg aspirin | 12 |
| clopidogrel | Day 1: a single 15-minute IV infusion of 0.025 mg/kg Day 7-9: 15-minute IV infusion of 0.025 mg/kg, TID, Q3 h* | Day 2: 300 mg clopidogrel Day 3-9: 75 mg aspirin | 12 |
| apixaban | Day 1: a single 15-minute IV infusion of 0.025 mg/kg Day 5-7: 15-minute IV infusion of 0.025 mg/kg, TID, Q3 h* | Day 2-7: 5mg apixaban, BID, Q12 h** | 12 |
| dabigatran | Day 1: a single 15-minute IV infusion of 0.025 mg/kg Day 5-7: 15-minute IV infusion of 0.025 mg/kg, TID, Q3 h* | Day 2-7: 110 mg dabigatran, BID, Q12 h** | 12 |

*three times a day, the 2nd dose is supposed to be taken 3 hours after the time of the first dose and the 3rd dose is supposed to be taken 3 hours after the time of the 2nd dose
**twice a day the 2nd dose is supposed to be taken 12 hours after the time of the first dose Endpoints Nature and severity of AEs and number of subjects with AEs Changes from baseline in physical examination, vital signs, ECG assessment, oximetry, coagulation, and clinical laboratory tests.

Plasma PK parameters of DC009

Plasma PK parameters of aspirin, clopidogrel, apixaban and dabigatran.

Results

DC009 drug product was generally safe and well tolerated when administered alone and in combination with aspirin, clopidogrel, apixaban or dabigatran.

The reported TEAEs were mild in severity, none were serious, and none led to the withdrawal of subjects from the study. The most-commonly reported TEAEs were irregular menstruation, abdominal pain, oral herpes, and headache in Part A and abdominal pain and headache in Part B of the study. There were no TEAEs related to the abnormal laboratory results. No clinically significant changes were reported for laboratory parameters (hematology, clinical comparison included $AUC_{0-t}$ and $C_{max}$. The results show that 3-day TID administration of DC009 drug product resulted in a mean $C_{max}$ of 48.86 ng/mL, and a maximum $C_{max}$ of 95 ng/mL, which is a safe level of plasma accumulation in subjects.

Example 14. Study 201: Phase 2, Single-Dose Study in Patients with Acute Ischemic Stroke The objective of this Phase 2, double-blind, single-dose, randomized, placebo-controlled study is to evaluate the safety, tolerability, and potential efficacy of DC009 drug product in patients with Acute Ischemic Stroke (AIS). The safety and potential efficacy outcomes from this Phase 2 study will guide the design of future studies in patients with acute ischemic stroke. Eligible patients will be randomized 2:1 to receive DC009 drug product or placebo via a 15-minute IV infusion to obtain a total of approximately 24 evaluable patients. Eligible patients will receive a single 0.025 mg/kg dose of DC009 drug product or placebo within 24 hours after the onset of stroke symptoms.

TABLE 13

| Dose Level (mg/kg) | Administration Time | Subject No. | Treatment Window |
| --- | --- | --- | --- |
| 0.025 mg/kg | A single dose 15-minute IV infusion | 16 | Within 24 hours after stroke symptom onset |
| Placebo | A single dose 15-minute IV infusion | 8 | Within 24 hours after stroke symptom onset | chemistry, and urinalysis), vital signs, ECG, and pulse oximetry results in any part of the study.

DC009 drug product has a limited effect on coagulation when co-administrated with apixaban and dabigatran. DC009 drug product has a limited effect on COL/ADP and COL/EPI when co-administrated with aspirin and clopidogrel.

In the case of all population (N=12), the mean $C_{max}$ for DC009 drug product was 40.14 ng/mL at Day 1 and 48.86 ng/mL at Day 3. The peak plasma concentration of DC009 drug product was achieved at 10-15 min post dose and DC009 drug product started eliminating 15 min post dose. In case of the Chinese population (N=6), the mean $C_{max}$ for DC009 drug product was 37.30 ng/mL at Day 1 and 40.00 ng/mL at Day 3. In case of the non-Asian population (N=6), the mean $C_{max}$ for DC009 drug product was 42.98 ng/mL at Day 1 and 57.72 ng/mL at Day 3. The mean $AUC_{0-last}$, $C_{trough}$, and $T_{max}$ for DC009 drug product were comparable across the Chinese and non-Asian populations.

TABLE 12

| Dose: 0.025 mg/kg (N = 12) | Day 1 1st dose | Day 3 9th dose |
| --- | --- | --- |
| $AUC_{0-last}$ (ng * hr/mL) Mean ± SD | 9.258 ± 2.797 | 11.87 ± 3.364 |
| $C_{max}$ (ng/mL) Mean ± SD | 40.14 ± 12.5 | 48.86 ± 17.06 |
| Maxima $C_{max}$ (ng/ml) | 57.50 | 95.00 |

To investigate whether the dose of DC009 was accumulated in multiple dose regimen, the potential dose accumulation effect was assessed by comparing PK parameters of the first dose and the last dose in the multi-day TID regimen of DC009. The comparisons were conducted on occasions when DC009 was alone or was co-administrated with aspirin, clopidogrel, apixaban, or dabigatran. PK parameters for The key inclusion criteria are as follows: Subject a) are to be aged 18-90 years, inclusive, at the time of screening, b) have a NIHSS of 4-30, c) clinical diagnosis of AIS within 24 hours after stroke symptom onset.

Tissue plasminogen activator (alteplase) is the only approved drug treatment for stroke in the US and, per the labeling, must be administered within 3 hours of stroke symptom onset. The approved window of administration in other countries varies. Because there is no approved drug treatment for acute ischemic stroke for administration beyond 3 hours of stroke symptom onset in the US, a placebo-controlled study would be ethically acceptable and is necessary in order to evaluate the drug effect objectively. Preliminary efficacy will be evaluated by assessing the infarct volume, occurrence of recurrent stroke, neurological outcome measured by NIHSS and functional independence measured by Modified Rankin Scale (mRS).

Primary Endpoint

The occurrence of symptomatic intracranial hemorrhage (sICH) within 36 hours after dosing, clinical deterioration defined as an increase in the NIHSS of 4 points or more and confirmed by computed tomography or magnetic resonance imaging.

Secondary Endpoint:

The occurrence of symptomatic intracranial hemorrhage (sICH) and asymptomatic intracranial hemorrhage (aICH) within 7 days after dosing The occurrence of mortality due to intracerebral or other major bleeding complications within 24 hours, 7 days, 30 days, and 90 days after dosing.

Number and severity of AEs within 90 days after dosing

The occurrence of recurrent stroke within 90 days after dosing

Functional outcome such as mRS

Neurological outcome such as NIHSS at 30 days

The change of infarct volume in CT or MRI examination at 24 hours and 7 days

Plasma PK parameters of DC009

Results

Baseline Characterization

TABLE 14

| Baseline | | DC009 (N = 16) | Placebo (N = 8) |
|---|---|---|---|
| Age | Mean ± SD | 62.1 ± 12.6 | 67.6 ± 9.2 |
| Onset to treatment | Median (hr, range) | 21 (7-24) | 18.5 (9-23) |
| time | Mean (hr, ±SD) | 17.9 ± 5.9 | 18.0 ± 5.0 |
| mRS | Median (range) | 4 (2-5) | 3.5 (2-5) |
| | Mean (±SD) | 3.9 ± 0.9 | 3.5 ± 1.1 |
| NIHSS | Median (range) | 6 (4-24) | 5 (4-17) |
| | Mean (±SD) | 10.1 ± 7.5 | 7.3 ± 4.8 |

Safety Results

No subject was reported with sICH during the study within 7 days. No subject died because of intracerebral or other major bleeding complications within 90 days. No subject died because of any reason within 30 days.

At Day 30, an increase in the NIHSS of ≥4 points was observed for 1 subject (14.3%) in the Placebo group and for no subject in DC009 drug product group.

Serious TEAEs were reported by 4 subjects (25%) in the DC009 drug product group and by 2 subjects (25%) in the Placebo group, all of which were considered as unrelated or unlikely related to investigational product. Among these 6 subjects, 2 subjects, one in each group died by Day 90 because of serious TEAEs.

All subjects in the Safety population reported with at least 1 TEAE, except 1 subject in the Placebo group. Most common TEAEs reported during the study included constipation reported by 10 subjects (62.5%) in the DC009 drug product group and 4 subjects (50.0%) in the Placebo group, and hypertension reported by 5 subjects (31.3%) in the DC009 drug product group and 2 subjects (25%) in the Placebo group. Most of the TEAEs reported during the study were either unrelated or unlikely related to the investigational product. No subject reported TEAE definitely related to the investigational product. Most of the TEAEs reported during the study were mild or moderate. No subject discontinued the investigational product because of a TEAE.

No clinically significant trend was observed for laboratory parameters, vital signs, ECGs, and neurological examinations.

Efficacy Results

Higher proportion of subjects in the DC009 drug product (46.7%) at Day 30 reported decrease in ≥4 NIHSS compared with the Placebo group (14.3%). It should be noted that NIHSS at Baseline was higher in the DC009 drug product group (10.1 [±7.45]) compared with the Placebo group (7.3 [±4.77]), implying NIHSS was not balanced at Baseline and subjects in the DC009 drug product group started with worse NIHSS.

TABLE 15

| NIHSS | DC009 drug product | Placebo |
|---|---|---|
| NIHSS improvement ≥ 4 points from baseline to day 30 (% subjects) | 47% | 14% |
| *Efficacy endpoint in the early clinical trial of IV | | |
| rtPA NIHSS improvement ≥ 4 points from baseline to day 30 + NIHSS ≤ 1 at day 30 (% subjects) | 47% | 29% |
| *Recommended endpoint for the early clinical trial in AIS | | |
| Change of NIHSS from baseline to day 30 (Mean ± SD) | −3.1 ± 2.8 | −1.1 ± 3.3 |
| Change of NIHSS from baseline to day 30 in patients with baseline NIHSS ≥ 6 (Mean ± SD) | −4.3 ± 3 | 3.5 ± 2.1 |

Figure 6:
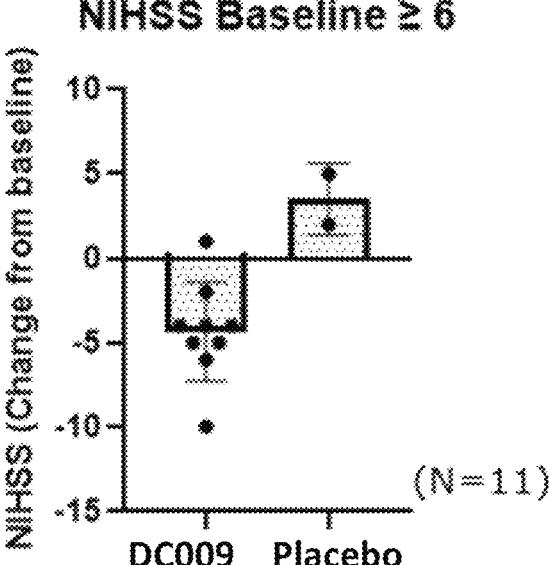
FIG. 6 shows the neurological improvement of DC009 in a human subject

FIG. 6 demonstrated the change of NIHSS score from baseline of a subpopulation with NIHSS baseline ≥6. The average score change was −4.3±3 score in DC009 drug product group, which indicated an improvement of neurological outcome, whereas, the average score change was 3.5±2.1 score in placebo group, which indicated a repression of neurological outcome. The result indicated the efficacy of DC009 drug product can be observed in the patient subpopulation with more severity of the neurological defect.

At Day 90, mRS of 0-1 was reported by 3 subjects (21.4%) in the DC009 drug product group and 1 subject (14.3%) in the Placebo group; mRS of 0-2 was reported by 7 subjects (50.0%) in the DC009 drug product group and by 3 subjects (57.2%) in the Placebo group. Proportion of subjects reporting mRS 0-2 was comparable between both the treatment groups at all visits. At Baseline poststroke, mRS of 4-5 was reported by 13 subjects (81.3%) in the DC009 drug product group and 4 subjects (50.0%) in the Placebo group. The mRS result is summarize in Table 16.

TABLE 16

| mRS | | DC009 | | Placebo | |
|---|---|---|---|---|---|
| Description | Score | Pre-dose | Day 90 | Pre-dose | Day 90 |
| Severe disability. Requires constant nursing care and attention, bedridden, incontinent | 5 | 81% | 21% | 50% | 29% |
| Moderate to severe disability. Unable to attend to own bodily needs without assistance, and unable to walk unassisted | 4 | | | | |
| Moderate disability. Requires some help, but able to walk unassisted | 3 | 6% | 29% | 25% | 14% |
| Slight disability. Able to look after own affairs without assistance, but unable to carry out all previous activities | 2 | 13% | 29% | 25% | 43% |

TABLE 16-continued

| mRS | | DC009 | | Placebo | |
|---|---|---|---|---|---|
| | | Pre- | | Pre- | |
| Description | Score | dose | Day 90 | dose | Day 90 |
| No significant disability. Able to carry out usual activities, despite some symptoms | 1 | 0% | 21% | 0% | 14% |
| No symptoms | 0 | | | | |

The result of Study 201 showed that DC009 drug product was safe and well-tolerated in subjects with AIS. DC009 drug product at the dose of 0.025 mg/kg shows efficacy compared to placebo group in treating AIS patient.

Example 15. Study 202: Phase 2, Multiple-Dose Study in Patients with Acute Ischemic Stroke The objective of this phase 2, double-blind, multiple-dose, randomized, placebo-controlled study is to evaluate the safety, tolerability, and potential efficacy of DC009 drug product in subjects with AIS.

TABLE 17

| Dose Level (mg/kg) | Administration Time | Subject No. | Treatment Window |
|---|---|---|---|
| 0.025 mg/kg | 30-minute IV infusion, BID, Q3-12 h*, 3 days | 1X | Within 24 hours after stroke onset |
| 0.05 mg/kg | 30-minute IV infusion, BID, Q3-12 h*, 3 days | 1X | Within 24 hours after stroke onset |
| Placebo | 30-minute IV infusion, BID, Q3-12 h*, 3 days | 1X | Within 24 hours after stroke onset |

*twice a day, the second dose of each day will be administered within 3-12 hours after the first dosing.

The key inclusion criteria are as follows: Subject a) are to be aged 18-80 years, inclusive, at the time of screening, b) have a NIHSS of 4-25, c) clinical diagnosis of AIS within 24 hours after stroke onset.
Safety Endpoint
    The occurrence of sICH and aICH after dosing
    The occurrence of mortality due to intracerebral or other major bleeding complications after dosing
    The occurrence of mortality after dosing
    Number and severity of AEs within 90 days after dosing
Primary Endpoint
    The ratio of patient with mRS 0-2
    The ratio of patient with a decrease in the NIHSS of 4 points or more and NIHSS ≤1 after dosing
Secondary Endpoint:
    Functional outcome such as the change of Modified Rankin Scale (mRS) at a specific period after dosing
    Neurological outcome such as the change of NIHSS compared to baseline at a specific period after dosing
    Activities of daily living and quality of life evaluated by Barthel Index at a specific period after dosing

Example 16. Study 203: Phase 2, Single- and Multiple-Dose Study in Patients with Acute Ischemic Stroke This study is a phase 2, two-parts, double-blind, randomized, placebo-controlled study is to evaluate the safety, and efficacy of DC009 drug product in subjects with AIS, where the subjects received endovascular thrombectomy (EVT).

The key inclusion criteria are as follows: Subject a) are to be aged 18-90 years, inclusive, at the time of screening, b) have a NIHSS of ≥6, c) eligible to be treated with EVT within 24 hours after stroke symptoms onset d) to receive the investigational product before EVT and within 24 hours after stroke symptoms onset e) confirmed to have a symptomatic intracranial occlusion, based on magnetic resonance angiography (MRA)/computed tomography angiography (CTA), at the following location: M1 middle cerebral artery (MCA), which is before bifurcation of M2 f) has Target Mismatch Profile on MRI (perfusion is included) or CTP: ischemic core volume ≤70 mL, mismatch ratio >1.2.

TABLE 18

| Part A design | | | |
|---|---|---|---|
| Dose Level (mg/kg) | Administration time | Subject No. | Treatment window |
| 0.025 mg/kg | 15-minute IV infusion, single dose | 2x | Within 24 hours after stroke symptom onset and before endovascular thrombectomy (EVT). |
| Placebo | 15-minute IV infusion, single dose | 1x | Within 24 hours after stroke symptom onset and before endovascular thrombectomy (EVT). |

The objective of Part A study is to determine the safety and efficacy of a single dose of DC009 drug product administered intravenously in subjects with acute ischemic stroke (AIS) undergoing endovascular thrombectomy (EVT).
Primary Endpoints
    The occurrence of sICH within 24 hours after the single dosing; clinical deterioration defined as an increase in the NIHSS of 4 points or more and confirmed by magnetic resonance (MR)/computed tomography (CT) imaging
Secondary Endpoints
(1) Safety outcomes
    The occurrence of sICH, aICH, and mortality
    The number and severity of AEs and the number of subjects with AEs
(2) Functional outcomes
    The proportion of subjects with independent functional outcome, defined as mRS ≤2 after dosing.
    The proportion of subjects with excellent functional outcome, defined as mRS ≤1 after dosing
    The shift of proportion of subjects with each grade on mRS from Baseline.
    The occurrence of recurrent stroke
(3) Neurological outcomes
    The proportion of subjects with neurological outcome improvement, defined as a decrease/change in NIHSS from Baseline
    The proportion of subjects with NIHSS ≤2 after dosing.

(4) Imaging outcomes

The change of infarct volume from Baseline by MRI/CTP.

The change of hypoperfusion lesion from Baseline by perfusion-weight imaging MRI/CTP.

The proportion of subjects with 90% reduction in hypoperfusion lesion from Baseline by perfusion-weight imaging MRI/CTP.

The recanalization rates before and post EVT procedure.

The proportion of subjects with complete recanalization/substantial angiographic reperfusion, defined as modified Treatment in Cerebral Infarction (mTICI) ≥2b at post EVT procedure.

TABLE 19

| Part B design | | | |
|---|---|---|---|
| Dose Level (mg/kg) | Administration time | Subject No. | Treatment window |
| 0.025 mg/kg | 15-minute IV infusion, BID, Q3-12 h, 3 days* | 2x | Within 24 hours after stroke symptom onset, the first dose of DC009 will be administrated before endovascular thrombectomy (EVT). |
| Placebo | 15-minute IV infusion, BID, Q3-12 h*, 3 days* | 1x | Within 24 hours after stroke symptom onset, the first dose will be administrated before endovascular thrombectomy (EVT). |

*twice a day, the second dose of each day will be administered within 3 to 12 hours after the first dosing.

The objective of Part B study is to determine the efficacy and safety of multiple doses of DC009 drug product in subjects with AIS undergoing EVT.

Primary Endpoints

The proportion of subjects with neurological outcome improvement, defined as a decrease in NIHSS of 4 points or more from Baseline.

Secondary Endpoints (1) Functional Outcomes:

The proportion of subjects with independent functional outcome, defined as mRS ≤2 after the first dosing.

The proportion of subjects with excellent functional outcome, defined as mRS ≤1 after dosing The shift of proportion of subjects with each grade on mRS from Baseline.

(2) Neurological Outcome

The proportion of subjects with neurological outcome improvement, defined as a decrease/change in NIHSS from Baseline.

The proportion of subjects with NIHSS ≤2 after the first dosing.

(3) The Occurrence of Recurrent Stroke (4) The Change of Cognition Assessment by Montreal Cognitive Assessment (MoCA) from Baseline.

(5) Imaging Outcomes

The change of infarct volume from Baseline by MRI/CTP.

The change of hypoperfusion lesion from Baseline by perfusion-weight imaging MRI/CTP.

The proportion of subjects with 90% reduction in hypoperfusion lesion from Baseline by perfusion-weight imaging MRI/CTP.

The recanalization rates before EVT procedure, post-EVT, 24 hours, and 7 days.

The proportion of subjects with complete recanalization/substantial angiographic reperfusion, defined as mTICI ≥2b at post EVT procedure.

(6) Safety Outcomes

The occurrence of sICH and aICH

The occurrence of mortality.

The number and severity of AEs and the number of subjects with AEs.

Example 17. Study 205 Phase 2, Multiple-Dose Study in Patients with Acute Ischemic Stroke The objective of this phase II, double-blind, randomized, placebo-controlled study to evaluate the safety and efficacy of multiple doses of DC009 drug product in subjects with Acute Ischemic Stroke (AIS).

TABLE 20

| Dose Level (mg/kg) | Administration Time | Subject No. | Treatment Window |
|---|---|---|---|
| 0.05 mg/kg | 30-minute IV infusion, BID, Q3-12 h, 3 days | 1x | The first dose of DC009 is administrated within 24 hours after stroke symptom onset |
| Placebo | 30-minute IV infusion, BID, Q3-12 h, 3 days | 1x | The first dose of placebo is administrated within 24 hours after stroke symptom onset |

* Twice a day, the second dose of each day will be administered within 3 to 12 hours after the first dosing.

The key inclusion criteria are as follows: Subject a) are to be aged 18-90 years, inclusive, at the time of screening, b) have a NIHSS of 6-25, c) has Target Mismatch Profile on MRI or CTP: ischemic core volume ≤70 mL, mismatch ratio >1.2 and mismatch volume ≥5 mL Primary Endpoints the proportion of subjects with Treatment Emergent Adverse Events (TEAEs), judged to be probably or definitely related to DC009 drug product within 90 days after the 1st administration.

Secondary Endpoints (1) Functional Outcomes

The proportion of subjects with mRS ≤2 after the 1st administration.

The proportion of subjects with mRS ≤1 after the 1st administration.

The shift of proportion of subjects with each grade on mRS after the 1st administration from Baseline.

(2) Neurological Outcome

The proportion of subjects with NIHSS ≥4 points from Baseline.

The proportion of subjects with neurological outcome improvement, defined as a decrease in NIHSS ≥4 points or NIHSS of 0 to 1 point after the 1st administration from Baseline.

The proportion of subjects with NIHSS ≤2 and NIHSS ≤1.

Change in NIHSS after the 1st administration from Baseline.

The occurrence of recurrent stroke.

The change of cognition assessment by Montreal Cognitive Assessment (MoCA) from Baseline.

(c) Imaging Outcomes

The change of infarct volume from Baseline by MRI/CTP.

The change of hypoperfusion lesion from Baseline by perfusion-weight imaging RI/CTP.

The proportion of subjects with 90% reduction in hypoperfusion lesion from Baseline by perfusion-weight imaging MRI/CTP.

(d) Safety Outcomes

The occurrence of sICH and aICH; clinical deterioration defined as an increase NIHSS of 4 points or more AND confirmed by magnetic resonance (MIR)/computed tomography (CT) imaging.

The occurrence of mortality due to any reason after 1 st administration.

The number and severity of AEs and the number of subjects with AEs.

Example 18. Pharmacokinetics Study of DC009 Following a Single Intravenous Administration in Sprague Dawley Rat The plasma pharmacokinetics of DC009 was studied in SD Rat following a single IV bolus administration of DC009. Male SD rats were dosed with DC009 at 0.001, 0.01, 0.1, 1 and 10 mg/kg by intravenous bolus injection with a dose volume of 1 mL/kg (n=3 per treatment group).

TABLE 21

| Group | Treatment No. of Animals/ Gender | Test Article | Dose Level (mg/kg) | Route | Dose Volume |
|---|---|---|---|---|---|
| 1 | 3 Male | DC009 | 0.001 | IV | 1 mL/kg |
| 2 | 3 Male | | 0.01 | Bolus | |
| 3 | 3 Male | | 0.1 | | |
| 4 | 3 Male | | 1 | | |
| 5 | 3 Male | | 10 | | |
| Plasma Collection | pre-dose, 2 minutes, 5 minutes, 15 minutes, 30 minutes, 60 minutes, 120 minutes, 240 minutes after a single IV Bolus injection | | | | |

TABLE 22

| | Group | | | | |
|---|---|---|---|---|---|
| | 1* | 2* | 3 | 4 | 5 |
| | | | Dose Level (mg/kg) | | |
| | 0.001 | 0.01 | 0.1 | 1 | 10 |
| | | | Dose (nmole/kg) | | |
| | 1.5 | 15 | 15 | 1500 | 15000 |
| | Mean SD | Mean SD | Mean SD | Mean SD | Mean SD |
| $C_{max}$ (ng/mL) | 1.6  1.1 | 6.1  3.0 | 59.9  4.1 | 426.0  4.1 | 8117.2  1049.9 |
| $AUC_{last}$ (min * ng/mL) | 105.5  118.9 | 200.9  56.1 | 473.2  149.1 | 3165.1  200.4 | 56161.9  3854.8 |
| $AUC_{0-\infty}$ (min * ng/mL) | 113.0  128.4 | 242.4  96.9 | 498.7  167.7 | 3189.5  178.3 | 56199.0  3803.6 |

*In dosing group 1 and 2, some of the measured concentrations of plasma samples were less than 5 ng/mL (LLOQ, Lower Limit of Qualification)

The results from dose of 0.1 to 10 mg/kg groups suggested that increasing doses of DC009 resulted in approximately dose-proportional increases in $C_{max}$ and $AUC_{0-\infty}$ in SD rats.

Example 19. Pharmaceutical Formulation, Dosage and Administration (for Examples 11-14)

The preparation of DC009 compound is disclosed in Example 63 of US Publication No. 2016-0083423.

DC009 drug product (Lyophilized Powder for Injection) is an injectable product that provided as preservative-free, sterile, lyophilized material in glass vials sealed with butyl rubber stoppers and flip-off aluminum crimp seals. Each vial contains DC009 drug substance, equivalent to 20 mg free base, as a lyophilized cake or powder. Placebo is formulated identically in the components, composition, and appearance to DC009 drug product but does not contain the active compound.

In the manufacturing of DC009 drug product, mannitol is first dissolved in Water for Injection (WFI) followed by the addition of hydrochloride salt of DC009 ($C32H51N7O8\cdot3HCl$). After adjusting to pH 4.5, the solution is diluted to target weight with WFI and the solution is checked for osmolality before being sterilized by aseptic filtration with a 0.2 μm PVDF filter. The pre-formulation contained 10 mg/mL DC009 and 3.8 w/w % of mannitol. After each vial is filled to the target weight within ±2%, the vials are capped half-way with a 20-mm stopper and placed in a tray for the lyophilizer. After the freeze-drying cycle is completed, the vacuum is broken with nitrogen to provide an inert headspace in the finished drug product.

DC009 drug product is reconstituted prior to use with 0.9% normal saline to 4 mg/mL, and is further diluted to suitable concentration with normal saline and administered by IV infusion. In Examples 11-14, suitable amount of drug product was diluted to 90 mL and the infusion volume was 60 mL.

In Examples 15-17, the pharmaceutical formulation, dosage, and administration of DC009 are similar to those described above, except the amount of DC009 drug substance in per drug product vial, the saline dilution factor, and the infusion volume may be modified according to common practice.

The invention, and the manner and process of making and using it, are now described in such full, clear, concise and exact terms as to enable any person skilled in the art to which it pertains, to make and use the same. It is to be understood that the foregoing describes preferred embodiments of the present invention and that modifications may be made therein without departing from the scope of the present invention as set forth in the claims. To particularly point out and distinctly claim the subject matter regarded as invention, the following claims conclude the specification.

What is claimed is:

1. A method for treating acute ischemic stroke in a human subject, comprising administering DC009 compound to the subject in need thereof,

DC009 wherein the DC009 dose is about 0.01-0.075 mg/kg/dose, and is administered at dosage intervals of about 3-12 hours.

2. The method of claim 1, wherein the DC009 dose is about 0.025-0.05 mg/kg/dose.

3. The method of claim 2, wherein the dose is about 0.025 mg/kg/dose.

4. The method of claim 2, wherein the DC009 dose is about 0.05 mg/kg/dose.

5. The method of claim 1, wherein the DC009 compound is administered twice a day.

6. The method of claim 1, wherein the DC009 compound is administered for 2 days or for 3 days.

7. The method of claim 4, wherein the DC009 compound is administered at least twice a day for 3 days.

8. The method of claim 1, wherein the DC009 compound is administered to the subject immediately or within 1-24 hours after the onset of acute ischemic stroke.

9. The method of claim 1, wherein the DC009 compound is administered by intravenous infusion or bolus injection.

10. The method of claim 9, wherein the DC009 compound is administered by intravenous infusion.

11. The method of claim 9, wherein the DC009 compound is administered by intravenous infusion over a period of 5-60 minutes.

12. The method of claim 1, further comprising administering aspirin, clopidogrel, apixaban or dabigatran to the subject.

13. The method of claim 1, wherein the Cmax in the plasma of the subject after dosing is less than 200 ng/ml.

* * * * *